(12) United States Patent
Kim et al.

(10) Patent No.: US 11,744,496 B2
(45) Date of Patent: Sep. 5, 2023

(54) METHOD FOR CLASSIFYING MENTAL STATE, SERVER AND COMPUTING DEVICE FOR CLASSIFYING MENTAL STATE

(71) Applicant: HAII Corp., Seoul (KR)

(72) Inventors: Jaejin Kim, Seongnam-si (KR); Chanhyung Kim, Seoul (KR); Seounguk Ha, Seoul (KR); Hoyoung Kim, Seoul (KR); Hunyeop Jeong, Hanam-si (KR); Jeehyun Han, Seoul (KR); Museok Kang, Seoul (KR); Jinhwan Oh, Seoul (KR); Yunyoung Cho, Seoul (KR); Sangho Jin, Incheon (KR); Jeongsang Yoo, Seoul (KR)

(73) Assignee: HAII Corp.

( * ) Notice: Subject to any disclaimer, the term of this patent is extended or adjusted under 35 U.S.C. 154(b) by 0 days.

(21) Appl. No.: 18/091,514

(22) Filed: Dec. 30, 2022

(65) Prior Publication Data
US 2023/0225653 A1 Jul. 20, 2023

(30) Foreign Application Priority Data

Jan. 20, 2022 (KR) .................. 10-2022-0008710

(51) Int. Cl.
*G16H 50/20* (2018.01)
*A61B 5/16* (2006.01)
(Continued)

(52) U.S. Cl.
CPC ............ *A61B 5/165* (2013.01); *A61B 5/0077* (2013.01); *A61B 5/02405* (2013.01);
(Continued)

(58) Field of Classification Search
None
See application file for complete search history.

(56) References Cited

U.S. PATENT DOCUMENTS

2021/0188291 A1* 6/2021 el Kaliouby ........... G16H 50/20

FOREIGN PATENT DOCUMENTS

| KR | 10-2011-0055215 | 5/2011 |
| KR | 10-2019-0076906 | 7/2019 |

(Continued)

OTHER PUBLICATIONS

Forbes M. et al., The Great Recession and Mental Health in the United States, Clinical Psychological Science, vol. 7, No. 5, 2019, pp. 900-913.
(Continued)

*Primary Examiner* — Ankit D Tejani
(74) *Attorney, Agent, or Firm* — Pandiscio & Pandiscio

(57) ABSTRACT

A method of classifying a mental state of a user using a computing device, which includes a microphone, a camera, a display, a wireless communication unit, and a processor, and a mental state classification server is provided. The method comprises: by the microphone, detecting ambient noise of the user; by the camera, generating an image by photographing a face of the user; by the processor, checking whether each of ambient noise of the user, ambient brightness of the face of the user obtained from the image, and a face position of the user obtained from the image is suitable for a heart rate variability measurement environment; by the processor, controlling to display on the display images indicating whether each of the ambient noise, the ambient brightness, and the face position is suitable for the heart rate variability.

15 Claims, 12 Drawing Sheets

(51) Int. Cl.
  *A61B 5/00* (2006.01)
  *A61B 5/024* (2006.01)
  *G16H 10/20* (2018.01)

(52) U.S. Cl.
  CPC .......... *A61B 5/7435* (2013.01); *G16H 10/20* (2018.01); *G16H 50/20* (2018.01)

(56) References Cited

FOREIGN PATENT DOCUMENTS

| KR | 10-2111852 | 12/2019 |
| KR | 10-2200816 | 1/2021 |
| KR | 10-2214402 | 2/2021 |
| KR | 10-2277820 | 7/2021 |
| KR | 10-2015-0059631 | 11/2021 |

OTHER PUBLICATIONS

Choi M. et al., The Effects of Neurofeedback Training on Physical, Psychoemotional Stress Response and Self-regulation for Late Adolescence: A Non-Randomized Trial, J Korean Acad Nurs, vol. 48, No. 2, 2008, pp. 208-220. (w/ English Abstract).

Horley K. et al., Face to face: visual scanpath evidence for abnormal processing of facial expressions in social phobia, Psychiatry Research, vol. 127, 2004, pp. 43-53.

Horley K. et al., Social Phobics do not see eye to ey: A visual Scanpath study of emotional expression processing, Journal of Anxiety Disorders, vol. 17, 2003, pp. 33-44.

Kim D. et al., A Preliminary Study on the Biased Attention and Interpretation in the Recognition of Face-Body Compound of the Individuals with Social Anxiety, Frontiers in Psychology, vol. 7, Article 414, Mar. 2016, pp. 1-10.

Kim W. et al., The Impact of Major Depressive Disorder on Productivity in Workers: A Preliminary Study Using WHO-HPQ(Health and Work Performance Questionnaire), J Korean Neuropsychiatr Assoc, vol. 46, No. 6, Nov. 2007, pp. 587-595. (w/ English Abstract).

Oh J. et al, Analysis of Previous Research on Heart Rate Variability and Stress Response by Environmental Stimulation, The Korean Society of Science and Art, vol. 38, Feb. 2020, pp. 231-241. (w/ English Abstract).

* cited by examiner

METHOD FOR CLASSIFYING MENTAL STATE, SERVER AND COMPUTING DEVICE FOR CLASSIFYING MENTAL STATE

REFERENCE TO PENDING PRIOR PATENT APPLICATION

This patent application claims benefit of Korean Patent Application No. 10-2022-0008710, filed Jan. 20, 2022, which patent application is hereby incorporated herein by reference.

FIELD OF THE INVENTION

The present disclosure relates to a mental state classification method, a mental state classification server, and a mental state classification computing device for classifying mental states, specifically, a method, a server, and a computing device for providing a classification service at least one mental state to a user.

BACKGROUND OF THE INVENTION

Over the past ten years, a number and cost of treatment for mental disorders has steadily increased, and a lifetime prevalence of seventeen mental disorders is 25.4%, indicating that one in four adults has experienced at least one mental disorder in their lifetime. In addition, according to the same survey, the number of psychiatric treatments related to youth and women has steadily increased over the past five years, which is attributed to the high stress and low socioeconomic level of the corresponding generation. Therefore, in consideration of social cost of mental illness, prevention, early detection, and early treatment are of utmost importance.

Moreover, as COVID-19 epidemic is prolonged, the increase in the number of psychiatric patients is accelerating, and one of the causes, 'anxiety about a rapid economic recession and a surge in the unemployment rate', can be considered to have been caused by employment shock after COVID-19 incident. In this regard, according to a study by Forbes, M. K., & Krueger, R. F. (*The Great Recession and mental health in the United States. Clinical Psychological Science*, 7(5), 900-913.), depression and anxiety increased in many countries during a financial crisis, and rising income inequality due to rising unemployment adversely affects life expectancy and suicide rate.

On the other hand, according to the research paper (*J Korean Neuropsychiatr Assoc*/Volume 46, No 6/November, 2007), workers with major depression had more days of absenteeism and more early leave than workers without major depression, and workers with major depression were rated much lower in the evaluation of their job performance. In other words, it was suggested that the overall job performance was greatly deteriorated due to major depression. From this, it can be seen that emotional problems of workers have a great influence on productive capacity of workers.

Therefore, it is necessary to check and manage mental health of workers in order to increase productivity of a company. Moreover, it can be seen that its importance is growing in the midst of social difficulties caused by the recent pandemic of COVID-19.

On the other hand, in the prior art, in order to understand the mental state of the worker, a user wrote an answer to a questionnaire provided by a clinical expert; and the clinical expert directly classified the mental state of the user based on the answer written in the questionnaire.

However, since workers do not want to disclose their current mental state to an outside world or tend to reduce seriousness of the state, in many cases, workers were unable to answer honestly enough to express their actual mental state.

Moreover, if an environment in which the workers answer the questionnaire is inappropriate, that is, if the worker being nervous about meeting a clinical expert, the survey location being unfamiliar to the worker, the environment being too noisy to the worker, or an ambient light of the location being too dim or too bright, the workers fill out the answer in a psychologically unstable state, resulting in a great obstacle in accurately classifying the workers' mental state.

Accordingly, there is an urgent need to develop a technology capable of providing a mental state classification service in an environment suitable for measuring the mental state of workers in which workers can maintain a mentally stable state.

An object of the present disclosure is to provide a new method capable of providing accurate and highly reliable mental state classification service to a user in a non-face-to-face manner by providing a mental state classification method, a mental state classification server, and a mental state classification computing device.

Prior Disclosures (Patent Document 1) Korean Patent Registration No. 10-2111852

(Non-Patent Document 1) Forbes, M. K., & Krueger, R. F. The Great Recession and mental health in the United States. Clinical Psychological Science, 7(5), 900-913.

(Non-Patent Document 2) J Korean Neuropsychiatr Assoc/Volume 46, No 6/November, 2007.

(Non-Patent Document 3) Horley, K., Williams, L. M., Gonsalvez, C., & Gordon, E. (2003). Social phobics do not see eye to eye:: A visual scanpath study of emotional expression processing. Journal of anxiety disorders, 17(1), 33-44.

(Non-Patent Document 4) Horley, K., Williams, L. M., Gonsalvez, C., & Gordon, E. (2004). Face to face: visual scanpath evidence for abnormal processing of facial expressions in social phobia. Psychiatry research, 127(1-2), 43-53.

(Non-Patent Document 5) Kim, D. H., & Lee, J. H. (2016). A preliminary study on the biased attention and interpretation in the recognition of face-body compound of the individuals with social anxiety. Frontiers in psychology, 7, 414.

SUMMARY OF THE INVENTION

According to one aspect of the present disclosure, a method of classifying a mental state of a user using a computing device, which includes a microphone, a camera, a display, a wireless communication unit, and a processor, and a mental state classification server is provided. The method may comprises: by the microphone, detecting ambient noise of the user; by the camera, generating an image by photographing a face of the user; by the processor, checking whether each of ambient noise of the user, ambient brightness of the face of the user obtained from the image, and a face position of the user obtained from the image is suitable for a heart rate variability measurement environment; by the processor, controlling to display on the display images indicating whether each of the ambient noise, the ambient brightness, and the face position is suitable for the heart rate variability, based on a result of checking whether each of the ambient noise, the ambient brightness, and the face position is suitable for the heart rate variability measurement environment; by the processor, providing a questionnaire for classification of a mental state on the display in response to checking whether each of the ambient noise, the ambient brightness, and the face position is suitable for a heart rate variability measurement environment; by the processor, generating an image by capturing the face of the user by the camera while the user inputs an answer to the questionnaire; by the processor, controlling the wireless communication unit to transmit the generated image to the mental state classification server; by the mental state classification server, receiving the image generated from the computing device; by the mental state classification server, controlling to extract heart rate variability data from the generated image; and by the processor, controlling to display the face of the user on the display before providing the user with the questionnaire for classification of the mental state on the display and during the questionnaire.

According to one embodiment of the present disclosure, the generating an image by capturing the face of the user by the camera may include: by the processor, controlling to display on the display a noise-suitable image or a noise-unsuitable image indicating whether the ambient noise is suitable or not, depending on whether the ambient noise is suitable for the heart rate variability measurement environment; by the processor, controlling to display a brightness-suitable image or a brightness-unsuitable image indicating whether the ambient brightness is suitable or unsuitable for the display according to whether the ambient brightness is suitable for the heart rate variability measurement environment; and by the processor, controlling to display on the display a face position-suitable image or a face position-unsuitable image indicating whether the face position is suitable or unsuitable for the heart rate variability measurement environment according to whether the face position is suitable for the heart rate variability measurement environment.

According to one embodiment of the present disclosure, the controlling to display on the display images may further comprise: by the processor, controlling to display a notification text on the display according to whether each of the ambient noise, the ambient brightness, and the face position is suitable for the heart rate variability measurement environment.

According to one embodiment of the present disclosure, the providing a questionnaire for classification of a mental state may comprise: by the processor, controlling to display a state of the face of the user including at least a middle of a forehead and both cheeks on the display while conducting a questionnaire on the mental state of the user.

According to one embodiment of the present disclosure, the providing a questionnaire for classification of a mental state may comprise: by the processor, generating time information by measuring a time from when the question of the questionnaire is provided on the display to when the user's answer to the question is input through the display; and by the processor, controlling the display to display an inverse question for confirming whether the user has consistently answered the questionnaire during the questionnaire.

According to one embodiment of the present disclosure, after the controlling to extract heart rate variability data, the method may further comprise: by the processor, determining whether the answer of the user to the questionnaire is an insincere answer based on at least one of the time information and a rate of consistently answering the inverse question.

According to one embodiment of the present disclosure, after the determining whether the answer of the user to the questionnaire is an insincere answer, the method may further comprise: by the processor, displaying a question confirming reliability of the user's answer to the questionnaire on the display in response to the user's answer to the questionnaire determined as an insincere answer; and by the processor, controlling the display to display notification content that induces the user to retake the questionnaire in response to an answer that the reliability of the user's answer to the questionnaire is not high is input through the display.

According to one embodiment of the present disclosure, after the controlling to extract heart rate variability data, the method may further comprise: by the mental state classification server, obtaining a first numerical value indicating a possibility that the user corresponds to the mental state based on an answer to the questionnaire input by the user by executing a first algorithm; by the mental state classification server, obtaining a second numerical value indicating a possibility that the user corresponds to the mental state based on the heart rate variability data of the user extracted by executing a second algorithm; and by the mental state classification server, to obtain a third numerical value indicating a possibility that the user corresponds to the mental state based on the first numerical value and the second numerical value by executing a third algorithm.

According to other aspect of the present disclosure, a mental state classification server for classifying a mental state of a user through a user computing device is provided. Wherein the mental state classification server may be configured to: receive sound information detected by a user computing device; receive an image captured by the user computing device and generated; check whether each of ambient noise of the user, ambient brightness from the image, and a face position of the user in the image is suitable for a heart rate variability measurement environment, based on the received sound information and the received image; transmit a first control signal for controlling the user computing device to the user computing device based on a result of checking whether the heart rate variability measurement environment is suitable, wherein the first control signal is a control signal that causes the user computing device to display on the display of the user computing device images indicating whether each of the ambient noise, the ambient brightness, and the face position is suitable for the heart rate variability measurement environment; transmit a second control signal to the user computing device in response to checking that each of the ambient noise, the ambient brightness, and the face position is suitable for a heart rate variability measurement environment, wherein the second control signal causes the user computing device to display a questionnaire for classification of a mental state on the display; receive an image generated by capturing the face of the user from the user computing device while the user inputs an answer to the questionnaire through the user computing device; and extract heart rate variability data from the answers to the questionnaire and the received images.

According to one embodiment of the present disclosure, the mental state classification server may be configured to: based on the result of checking whether the heart rate variability measurement environment is suitable, transmit a 1-1 control signal to the user computing device to display a noise-suitable image or a noise-unsuitable image indicating whether the ambient noise is suitable or not; transmit a 1-2 control signal to the user computing device to display on the display a brightness-suitable image or brightness-unsuitable image indicating whether the ambient brightness is suitable or unsuitable; transmit a 1-3 control signal to the user computing device to display on the display a face position-suitable image or face position-unsuitable image indicating suitability or unsuitability of the face position.

According to one embodiment of the present disclosure, the mental state classification server maybe configured to: based on the result of checking whether the heart rate variability measurement environment is suitable, transmit a third signal to the user computing device to display on the display a notification text indicating whether each of the ambient noise, the ambient brightness, and the face position is suitable for the heart rate variability measurement environment.

According to another aspect of the present disclosure, a computing device for classifying a user's mental state is provided. The computing device may comprise: a microphone; a camera; a display; and a processor; wherein the microphone is configured to sense ambient noise of the user; wherein the camera is configured to generate an image by capturing the face of the user; wherein the processor is configured to check whether each of the ambient noise sensed by the microphone, the ambient brightness obtained from the image, and the face position obtained from the image is suitable for a heart rate variability measurement environment; control the display to display images indicating whether each of the user's ambient noise, the ambient brightness, and the face position is suitable for a heart rate variability measurement environment; display a questionnaire for classification of the user's mental state on the display in response to checking that each of the ambient noise, the ambient brightness, and the face position is suitable for the heart rate variability measurement environment; and extract a heart rate variability data from the image, which is generated by capturing the face of the user while the user inputs an answer to the questionnaire, and wherein the processor is configured to control the face of the user to be displayed on the display before displaying a questionnaire for classification of the mental state on the display and while the questionnaire is in progress.

According to one embodiment of the present disclosure, the proves is configured to control to display on the display a noise-suitable image or a noise-unsuitable image indicating whether the ambient noise is suitable or not, a brightness-suitable image or a brightness-unsuitable image indicating whether the ambient brightness is suitable or unsuitable, and a face position-suitable image or a face position-unsuitable image indicating whether the face position is suitable or unsuitable, based on the result of checking whether the heart rate variability measurement environment is suitable.

According to one embodiment of the present disclosure, the processor may be configured to control the display to display on the display a notification text indicating whether each of the ambient noise, the ambient brightness, and the face position is suitable for the heart rate variability measurement environment.

According to one embodiment of the present disclosure, the processor may be configured to control the display to display a progress rate of the heart rate variability measurement as a graph or numerical value while conducting a questionnaire on the mental state of the user.

According to one embodiment of the present disclosure, the method for classifying a mental state is advantageous in that it may not only extract heart rate variability with high accuracy that is close to the actual heart rate variability, but also classify the user's mental state with high reliability based on the user's response and the extracted heart rate variability, as it surveys and photographs the user's face in a stable state, in a suitable range of ambient noise, ambient brightness, and the location of the face captured by the camera that can create an environment in which the heart rate variability can be measured normally.

According to one embodiment of the present disclosure, the mental state classification server of the present disclosure is advantageous in that it may not only extract heart rate variability with high accuracy that is close to the actual heart rate variability, but also classify the user's mental state with high reliability based on the user's response and the extracted heart rate variability, as it surveys and photographs the user's face in a stable state, in a suitable range of ambient noise, ambient brightness, and the location of the face captured by the camera that can create an environment in which the heart rate variability can be measured normally.

According to one embodiment of the present disclosure, the computing device of the present disclosure is advantageous in that it may not only extract heart rate variability with high accuracy that is close to the actual heart rate variability, but also classify the user's mental state with high reliability based on the user's response and the extracted heart rate variability, as it surveys and photographs the user's face in a stable state, in a suitable range of ambient noise, ambient brightness, and the location of the face captured by the camera that can create an environment in which the heart rate variability can be measured normally.

DESCRIPTION OF THE INVENTION

Figure 1:
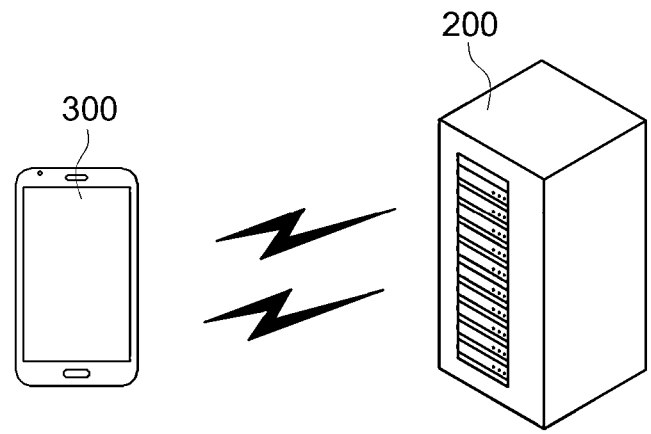
FIG. 1 is a diagram schematically illustrating a configuration of a mental state classification server and a computing device according to an embodiment of the present disclosure.

Hereinafter, with reference to the accompanying drawings, the embodiments of the present disclosure will be described in detail so that those of ordinary skill in the art to which the present disclosure pertains can readily implement them. However, the present disclosure may be implemented in several different forms and is not limited to the embodiments described herein.

In order to clearly explain the present disclosure in the drawings, parts irrelevant to the description are omitted, and similar reference numerals are attached to similar parts throughout the specification.

Throughout the specification, when a part "includes" or "comprises" a certain component, it means that other components may be further included, rather than excluding other components, unless otherwise stated.

It is to be understood that the techniques described in the present disclosure are not intended to be limited to specific embodiments, and include various modifications, equivalents, and/or alternatives of the embodiments of the present disclosure.

The expression "configured to (or set to)" as used in this disclosure, depending on the context, can be used interchangeably with, for example, "suitable for", "having the capacity to," "designed to," "adapted to," "made to," or "capable of". The term "configured (or configured to)" is not necessarily means only "specifically designed to" hardware. Instead, in some circumstances, the expression "a device configured to" means that the device is "capable of" with other devices or components. For example, the phrases "a processor configured (or configured to perform) A, B, and C," "a module configured (or configured to perform) A, B, and C", means a dedicated processor (for example, it may mean an embedded processor) or a generic-purpose processor (e.g., a CPU or an application processor) capable of performing corresponding operations by executing one or more software programs stored in a memory device.

Hereinafter, an embodiment of the present disclosure will be described with reference to the attached drawings. However, in the following description, to avoid unnecessarily obscuring the essentials of the present disclosure, detailed descriptions of well-known functions or configurations will be omitted in the following description.

Figure 2:
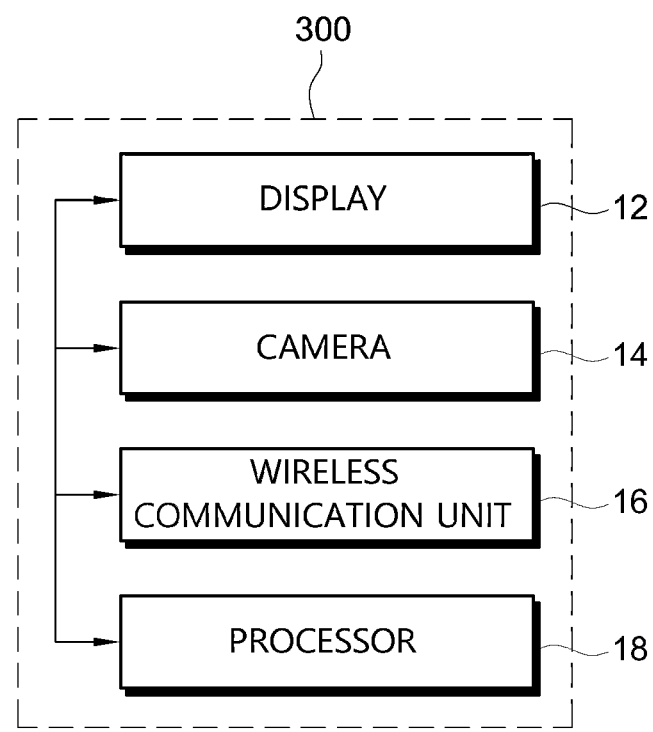
FIG. 2 is a conceptual diagram illustrating configurations of a computing device according to an embodiment of the present disclosure.
Figure 3:
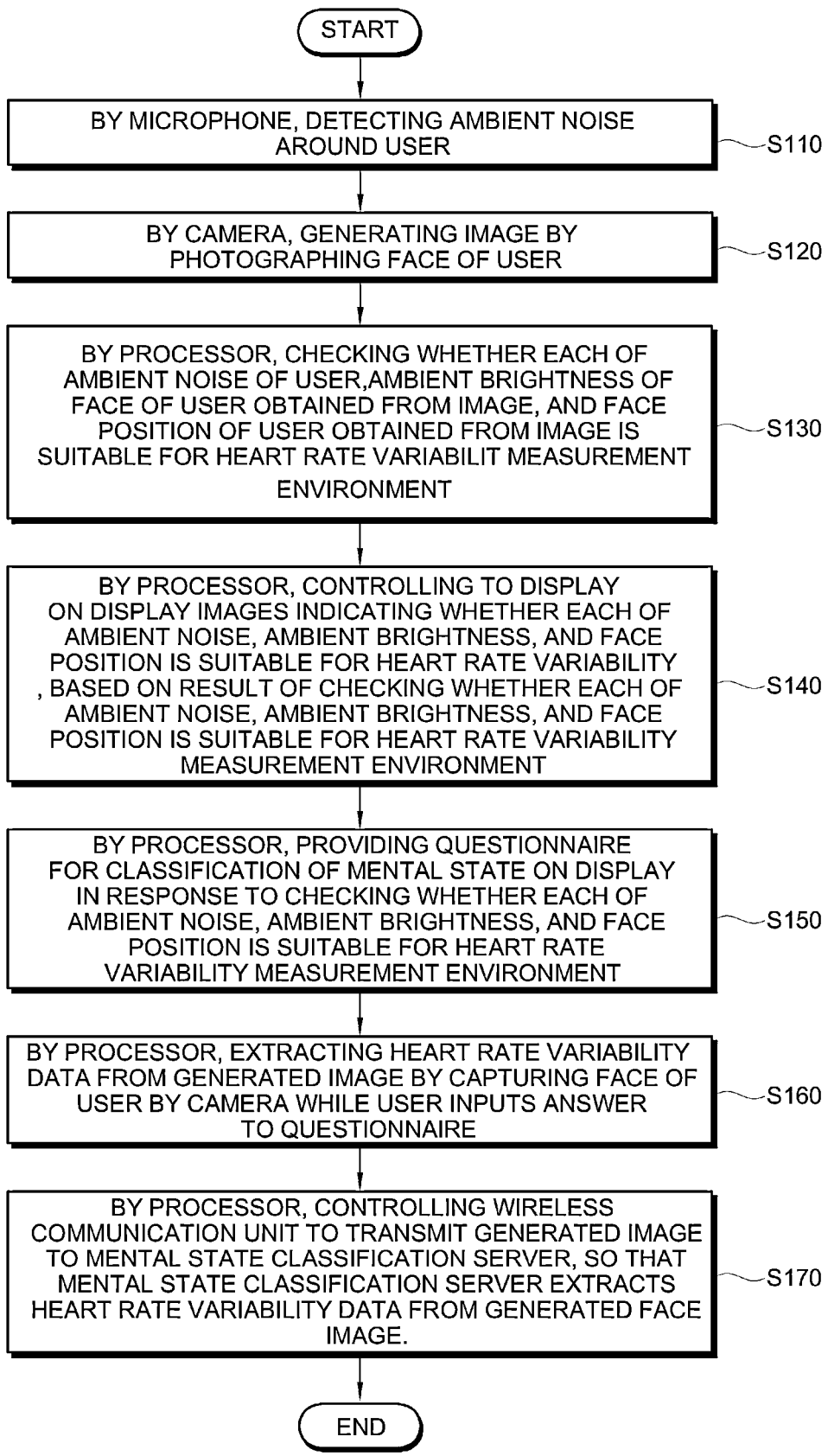
FIG. 3 is a flowchart illustrating steps of a mental state classification method according to an embodiment of the present disclosure.
Figure 4A:
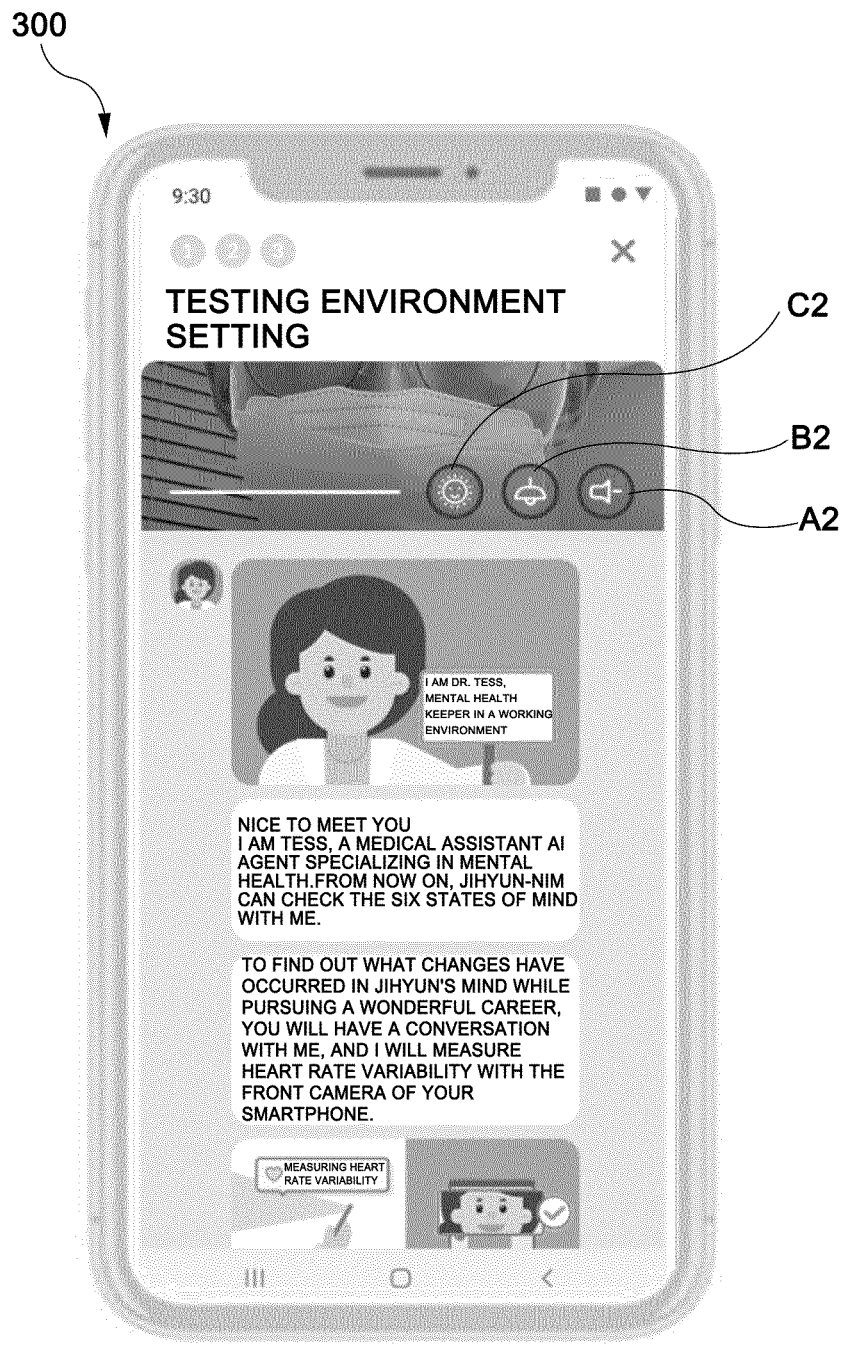
FIG. 4A, FIG. 4B, and FIG. 4C are diagrams illustrating a state in which a guide phrase is displayed to have a suitable environment for a heart rate variability measurement of a computing device according to another embodiment of the present disclosure.
Figure 4B:
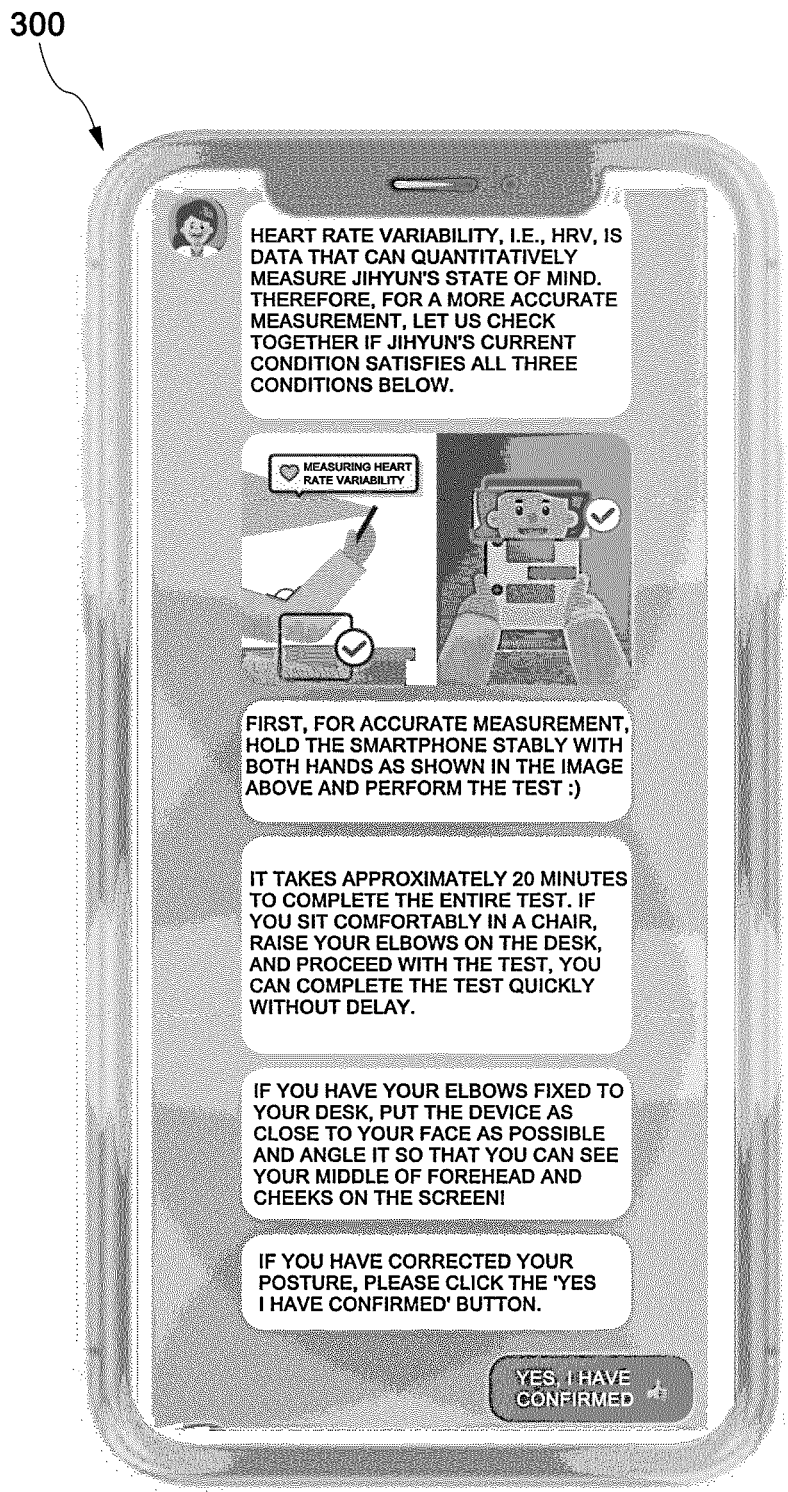
Figure 4C:
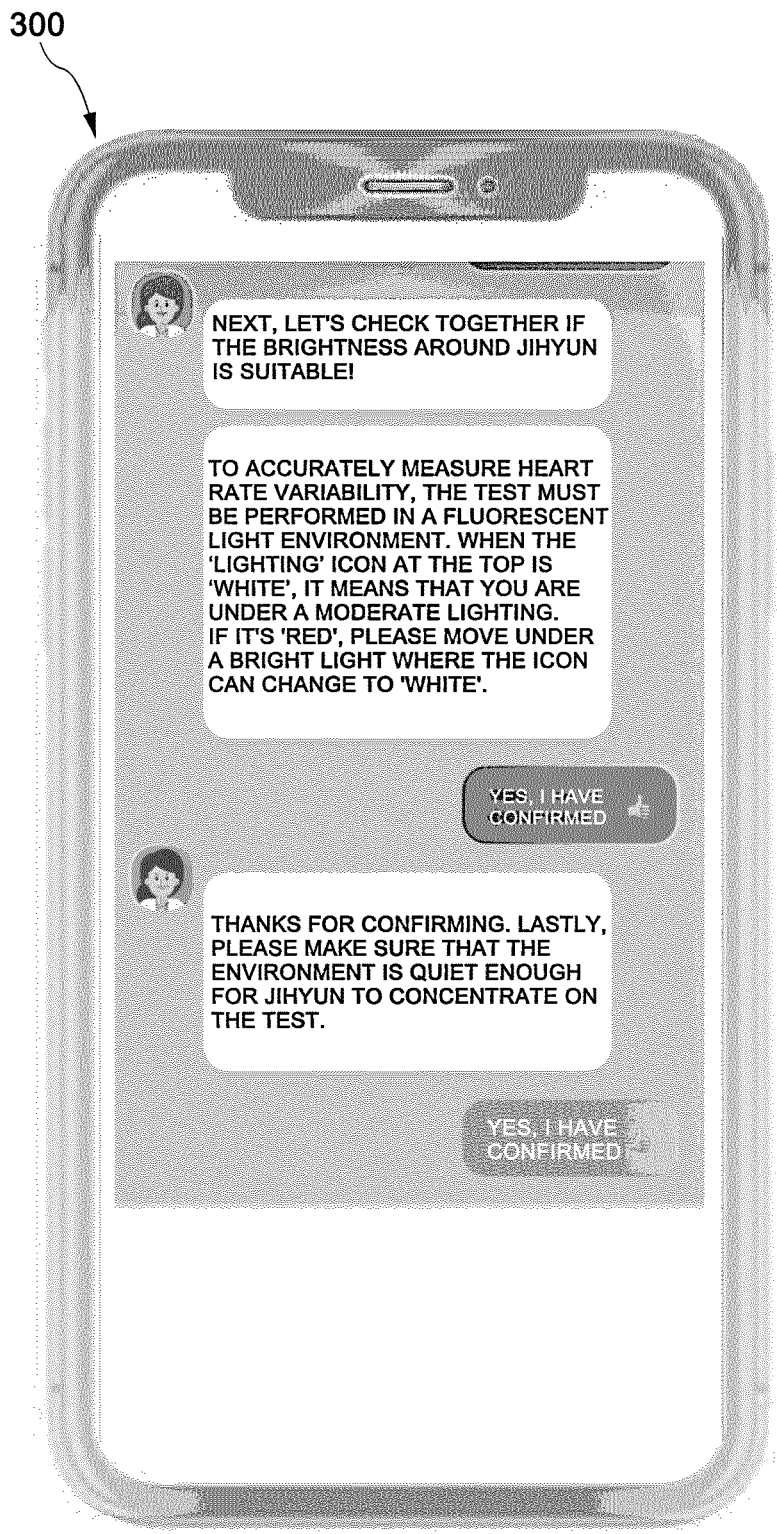

FIG. 1 is a diagram schematically illustrating a configuration of a mental state classification server 200 and a computing device 300 according to an embodiment of the present disclosure. FIG. 2 is a conceptual diagram illustrating configurations of a computing device 300 according to an embodiment of the present disclosure. FIG. 3 is a flowchart illustrating steps of a mental state classification method 100 according to an embodiment of the present disclosure. FIG. 4A, FIG. 4B, and FIG. 4C are diagrams illustrating a state in which a guide phrase is displayed to have a suitable environment for a heart rate variability measurement of a computing device 300 according to another embodiment of the present disclosure.

The computing device 300 includes a hardware on which a computing system operating program is executed, a software executed on the hardware, and a cloud service, and may be connected to each other or to other servers through a network. For example, the computing device 300 may be a smartphone.

Referring to FIG. 1 to FIG. 4C, the mental state classification method 100 according to an embodiment of the present disclosure may be a method of classifying mental state of a user though a computing device 300 comprising of a computing device 300 having a microphone 11, a camera 14, a display 12, a wireless communication unit 16, and a processor 18 and a mental state classification server 200.

The method of classifying a mental state of a user 100 comprises steps of, by microphone 11, detecting ambient noise around the user (S110); by camera 14, generating an image by photographing a face of the user (S120); by the processor 18, checking whether each of ambient noise of the user, ambient brightness of the face of the user obtained from the image, and a face position of the user obtained from the image is suitable for a heart rate variability measurement environment (S130); by the processor 18, controlling to display on the display 12 images indicating whether each of the ambient noise, the ambient brightness, and the face position is suitable for the heart rate variability, based on a result of checking whether each of the ambient noise, the ambient brightness, and the face position is suitable for the heart rate variability measurement environment (S140); by the processor 18, providing a questionnaire for classification of a mental state on the display 12 in response to checking whether each of the ambient noise, the ambient brightness, and the face position is suitable for a heart rate variability measurement environment (S150); by the processor 18, generating an image by capturing the face of the user by the camera 14 while the user inputs an answer to the questionnaire (S160); and, by the processor 18, controlling the wireless communication unit 16 to transmit the generated image to the mental state classification server 200, so that the mental state classification server 200 extracts heart rate variability data from the generated image (S170).

Further, the step of checking whether each position of the user's face obtained from the image is suitable for a heart rate variability measurement environment (S130) may include, by the processor 18, checking whether the user's ambient noise input from the microphone 11 is suitable for the heart rate variability measurement environment.

In another embodiment, the step of checking whether the heart rate variability measurement environment is suitable (S130) may include checking whether the ambient brightness of the user is suitable for the heart rate variability measurement environment by analyzing information on the ambient brightness of the user obtained through an illuminance sensor (not shown) provided in the computing device 300.

Here, heart rate variability (HRV) means the degree of variability of heart rate. That is, the heart rate variability means a minute change between one cardiac cycle and the next cardiac cycle. The heart rate is determined by an influence of an autonomic nervous system on an intrinsic spontaneity of the sinus node, which is related to an interaction between sympathetic and parasympathetic nerves. This interaction changes from moment to moment according to changes in an internal/external environment, which causes a change in the heart rate.

In addition, the heart rate variability measurement environment refers to a measurement environment capable of extracting the user's heart rate variability through an image of the user generated in real-time by photographing the user using the camera 14. In other words, it means an environment in which color changes generated through light reflected in blood vessels under a skin of the user's face can be clearly distinguished from the images generated through real-time photographing by the camera 14. Additionally, the heart rate variability measurement environment may further include an environment in which the user can maintain a psychologically stable state.

The questionnaire for classifying the mental state may be configured to classify a severity of at least one mental state. Here, the at least one mental state may include major depression disorder, anxiety disorder, adjustment disorder, PTSD, suicidal ideation, and insomnia. Accordingly, the questionnaire provided by the service platform 110 includes a questionnaire related to at least one of major depressive disorder, anxiety disorder, adjustment disorder, PTSD, suicidal ideation, and insomnia.

For example, clinical scales of mental states that can be used in the questionnaire are shown in Table 1 below.

TABLE 1

| Category | Name of mental state | Clinical questionnaire tool |
| --- | --- | --- |
| 1 | major depressive disorder | PHQ-9 (Patient Health Questionnaire 9) |
| 2 | anxiety disorder | GAD-7 (Generalized Anxiety Disorder 7) |
| 3 | adjustment disorder | ADNM-4 (Adjustment Disorder-New Module-4) |
| 4 | PTSD | K-PC-PTSD-5 (Korean version of the Primary Care PTSD Screen for DSM-5) |
| 5 | suicidal ideation | P4 (P4 Suicidality Screener) |
| 6 | insomnia | ISI (Insomnia Severity Index) |

Referring to FIG. 4A to FIG. 4C, the method of classifying a mental state 100, prior to the step of providing a questionnaire for classifying a mental state to the display 12 (S150), may further include, by the processor 18, a step of controlling the display 12 to display a guide phrase to lead the user to set surroundings to be suitable for the heart rate variability measurement environment. For example, the guide phrase may be "to accurately measure heart rate variability, the test must be performed under a fluorescent light environment.", "please make sure that the environment is quiet enough for Jihyun to concentrate on the test.", "place the device as close to your face as possible and adjust the angle so that you can see a middle of a forehead and cheeks on the screen!", "please hold the smartphone steady with both hands while taking the test.", etc.

Figure 5:
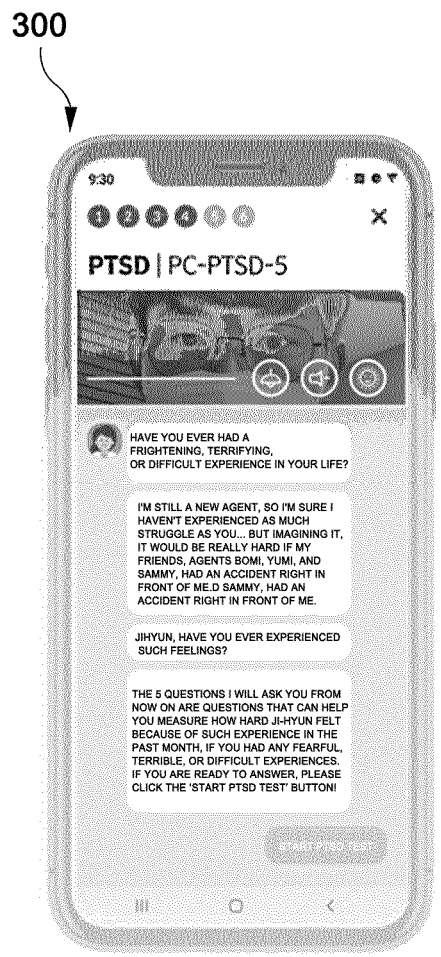
FIG. 5 is a diagram illustrating figures explaining a questionnaire to a user prior to a questionnaire for classifying a mental state of the user of a computing device according to an embodiment of the present disclosure.
Figure 6:
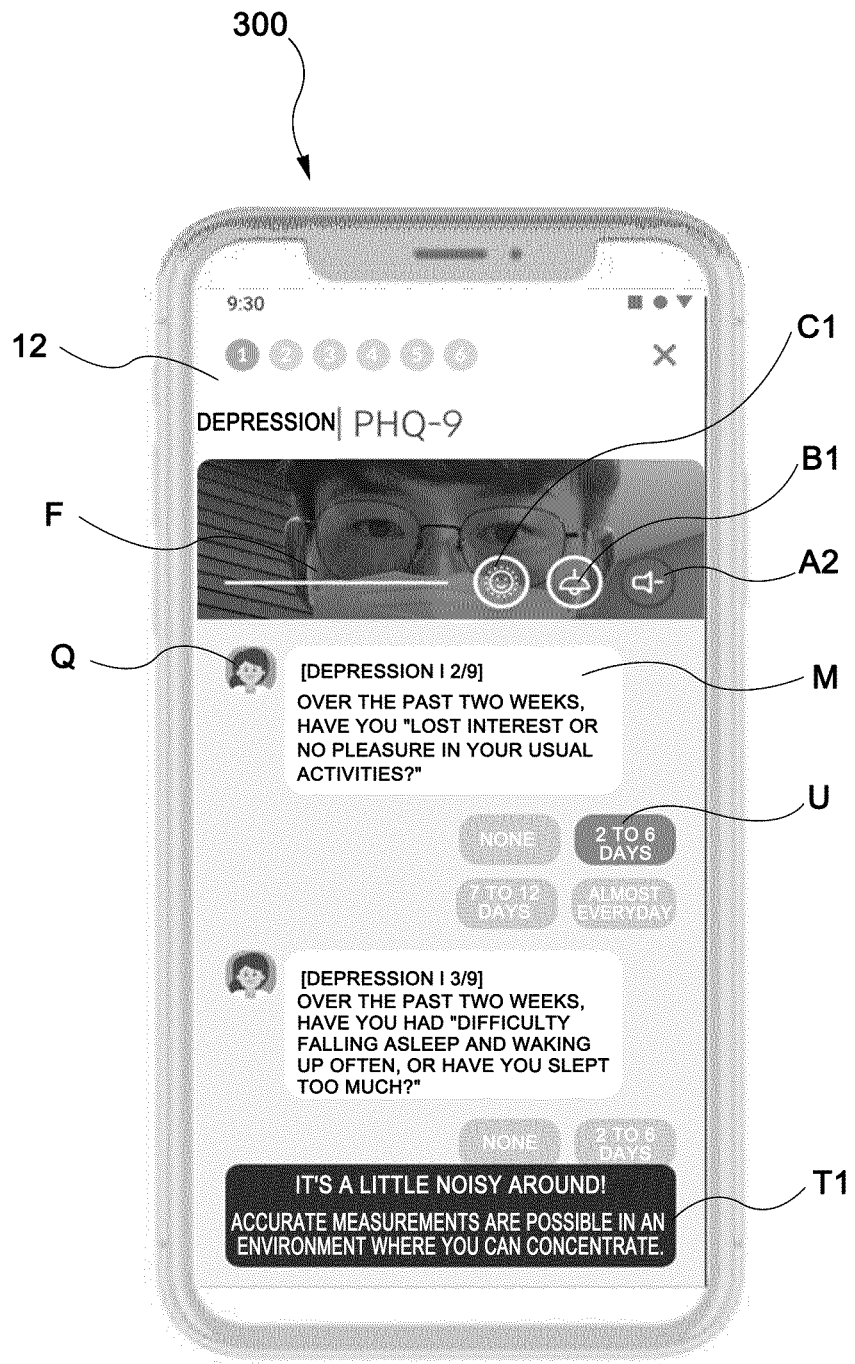
FIG. 6 to FIG. 8 are diagrams illustrating states conducting a questionnaire for classifying a mental state of a computing device according to an embodiment of the present disclosure.
Figure 7:
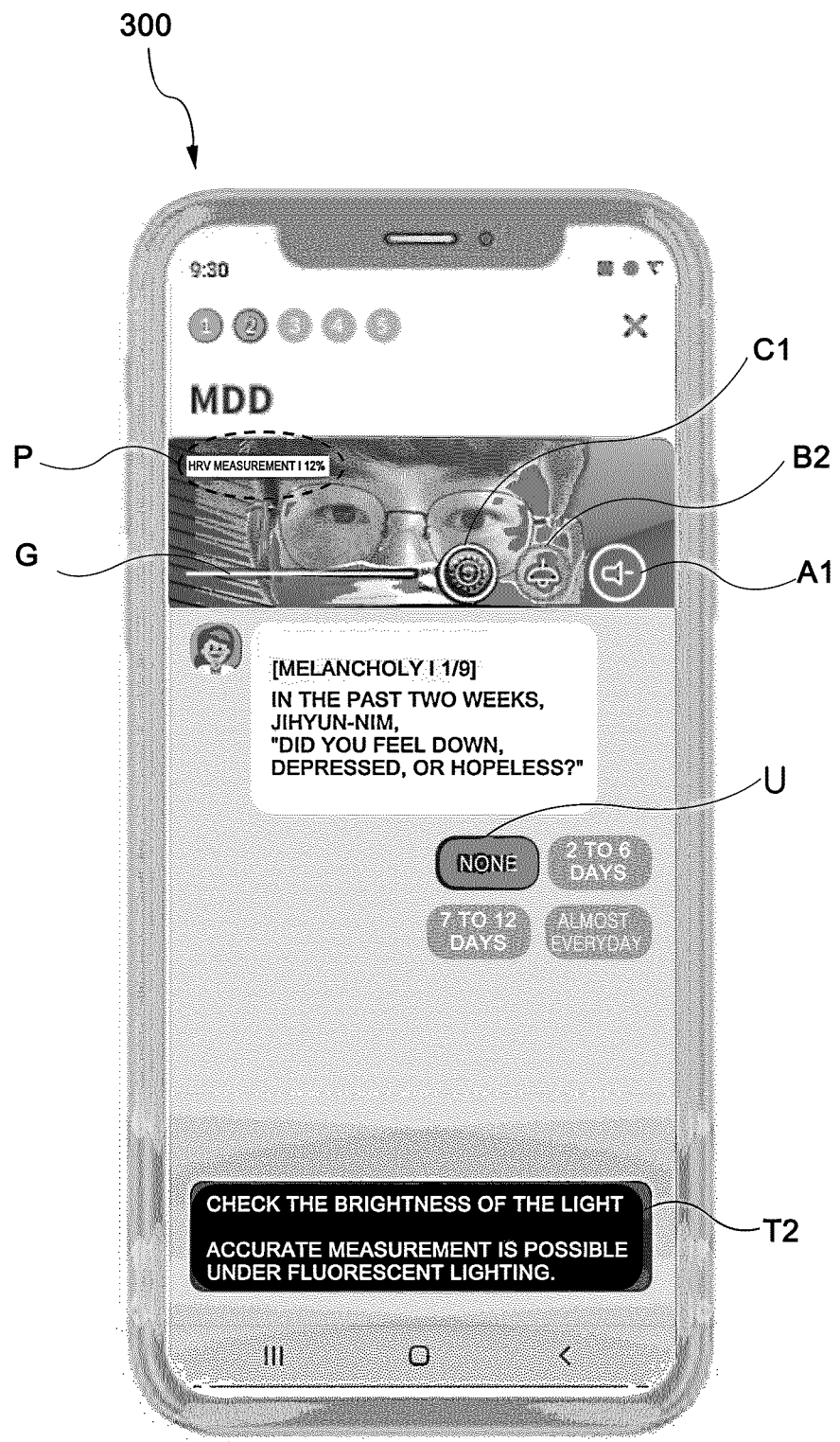
Figure 8:
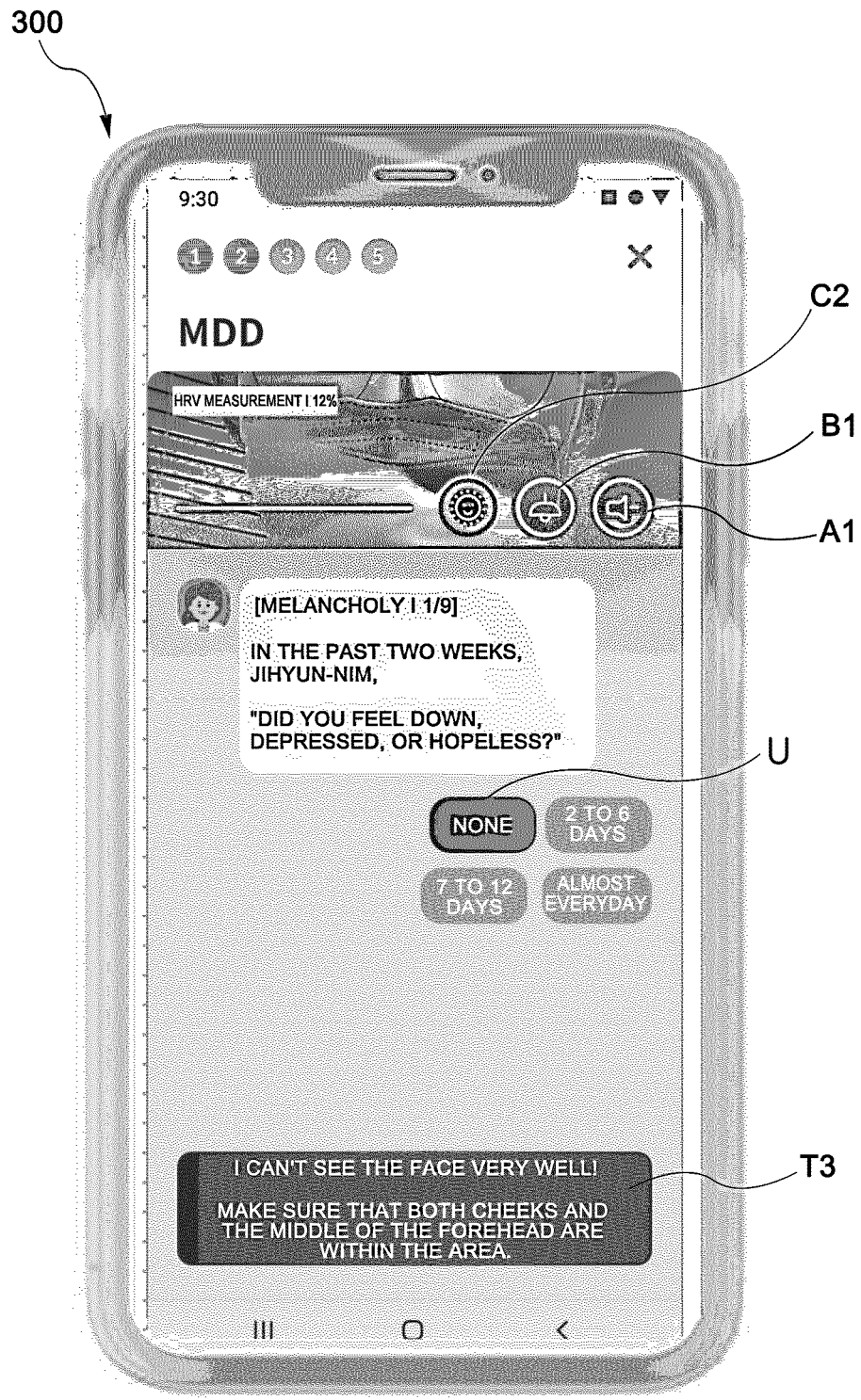

FIG. 5 is a diagram illustrating figures explaining a questionnaire to a user prior to a questionnaire for classifying a mental state of the user of a computing device according to an embodiment of the present disclosure. FIG. 6 to FIG. 8 are diagrams illustrating states conducting a questionnaire for classifying a mental state of a computing device according to an embodiment of the present disclosure.

The step of providing a questionnaire for classifying the mental state (S150) on the display 12 of the method for classifying mental state 100 may further include a step of providing questionnaire for classifying at least one mental state through an application program (i.e., an app) installed in the computing device 10. For example, as shown in FIG. 6, the application program can be configured so that, when it provides a questionnaire to the user computing device 300, the virtual person Q may deliver the questionnaire item M to the user in a form of a chat message. The application program may be configured so that the user inputs an answer to the question M of the questionnaire as a multiple-choice answer U.

Additionally, as shown in FIG. 5, the step of providing a questionnaire for classifying the mental state (S150) on the display 12 of the method for classifying mental state 100 may include, prior to providing of the questionnaire, a step of notifying the user of guidance such as "the questionnaire to be provided is a questionnaire about what kind of mental state", "number of questions the above questionnaire consist of", "conditions to be considered by users when answering the above questionnaire", etc.

Further, the step of providing a questionnaire for classifying the mental state (S150) on the display 12 of the method for classifying mental state 100 may further include a step of, by the processor 18, regarding the mental state to be classified, controlling a chatbot to display a conversation about an experience of his/her own mental state to the user to encourage the user's self-disclosure, on the display 12. For example, as shown in FIG. 5, the conversation about an experience of its own may be "It would be really difficult if my friend, agents Bomi, Yumi, and Semi, had an accident right in front of me."

In addition, the step of providing a questionnaire for classifying the mental state (S150) on the display 12 of the method for classifying mental state 100 may further include a step of, by the processor 18, controlling the display 12 to display a phrase explaining the purpose of the mental state classification service to prompt a sincere answer from the user. For example, the phrase explaining the purpose of the mental state classification service may be "this service is a service to check the user's mental health, and the data collected from it can be useful when the user applies for compensation for industrial accidents in the future."

Further, the step of providing a questionnaire for classifying the mental state (S150) on the display 12 of the method for classifying mental state 100 may further include a step of, by the processor 18, controlling the display 12 to display a conversation phrase so that that make a user feel like a chatbot has a persona of a medical professional. For example, the conversation phrase may be "hello employees! I am Tess, an AI agent assisting a psychiatric specialist. Now, let's check your mental health status with me." Accordingly, the mental state classification method 100 can induce a sincere answer from a user through the chatbot that converses as if having a persona of a medical expert.

In addition, the step of providing a questionnaire for classifying the mental state (S150) on the display 12 of the method for classifying mental state 100 may further include a step of, by the processor 18, controlling the display 12 to display an encouraging phrase so that the user can actively participate in the questionnaire. For example, the encouraging phrase may be, "you can check your mental health by using this service," or "you're almost done! Shall we keep it up?". Therefore, in the mental state classification method 100, the chatbot can deliver the encouraging phrase to the user to induce a sincere answer from the user.

For example, the step of providing a questionnaire for classifying the mental state (S150) on the display 12 may further include as step of, when classifying the user's multiple mental state, by the processor 18, controlling the display 12 to display a plurality of items for each mental state. The processor 18 may be an application processor 18. However, it is not necessarily limited to this embodiment, and the mental state classification method 100 of the present disclosure may be provided to the computing device 300 without notifying the user of which mental state the questionnaire is for. For example, the step of providing a questionnaire for classifying the mental state (S150) on the display 12 may further include a step of, by the processor 18, controlling the display 12 to display a questionnaire on the user's mental state of major depressive disorder without notifying the user that the questionnaire provided is intended to screen for major depressive disorder.

In one embodiment, the processor 18 may include application specific integrated circuits (ASICs), digital signal processors (DSPs), digital signal processing devices (DSPDs), programmable logic devices (PLDs), field programmable gate arrays (FPGAs), controllers (controllers), micro-controllers, microprocessors, or any other type of processor or controller for performing a function.

For example, the display 12 may be a touch pad. In this case, the user may input an answer by touching the display 12. Alternatively, the user may input an answer to the questionnaire through a microphone (i.e., voice input), a keyboard, and a keyboard application. For example, as shown in FIG. 7, the user may input an answer by clicking a button of a multiple-choice answer U corresponding to the answer to the questionnaire displayed on the display 12.

For example, a range suitable for the heart rate variability measurement environment of the ambient noise may be 20 decibels to 60 decibels. For example, a range suitable for the heart rate variability measurement environment of the ambient brightness may be 170 lux to 220 lux. For example, a range suitable for the heart rate variability measurement environment of the face position may be a range including a middle of a forehead and both cheeks of the user's face.

The step of controlling to extract the heart rate variability data (S160) may further include, by the processor 18, a step of obtaining, in real time, an image F generated by photographing the user's face with a camera 14 while the user inputs answers to the questionnaires. For example, when the computing device 300 is a smartphone, the camera 14 of the smartphone may be a front camera 14 located on top of the display 12 of the smartphone.

In one embodiment, the step of controlling to extract the heart rate variability data (S160) may include detecting a face using a deep learning model on a frame of an image received from the camera and extracting the heart rate variability data by analyzing the detected image. At this time, if the face is not detected, the step (S160) may include, in response to the fact that the face is not detected from the image, transmitting whether the face is detected to the terminal 10 and requesting the user to take a picture again and transmit.

The step of controlling to extract the heart rate variability data (S160), after detecting the face, may define a face to extract heart rate variability data. The step of defining the face may include defining facial regions for a forehead and cheek regions. The step of defining the face, for example, may use Viola-Jones algorithm to apply face points by dividing the Region of Interest (ROI) in shell units. Thus, it allows more robust tracking while minimizing computational costs.

The step of controlling to extract the heart rate variability data (S160) may develop a face tracking technology that integrates a Karhunen Loeve Transform (KLT) based tracking algorithm and an Affine transform and can perform tracking of the same object through a re-detection-based method when face tracking fails.

The step of controlling to extract the heart rate variability data (S160) may extract a color-based face fine movement signal by tracking a head movement by the fine movement and extracting a minute change in color accordingly.

The step of controlling to extract the heart rate variability data (S160) may normalize each motion signal and apply a band-pass filter to a heart rate band in order to remove noise other than a heart rate component from the extracted face motion signal.

In the face image received by the mental state classification server 200 in real time, different reflectance may be shown according to a wavelength length of each RGB color under the influence of a change in hemoglobin of blood vessels in the facial skin and a light reflected from a skin. Through this mechanism, it is possible to have minute color changes due to heartbeat in the face image. Here, basal differences of facial fine motion signals can be found. Since the basal difference of the face fine motion signal is independent of the heartbeat component, the step of controlling to extract the heart rate variability data (S160) performs a normalization operation of the fine movement signal to remove the basal difference of the fine movement signal of the face to match the base.

Application of the band filter refers to filtering the extracted face motion signal into a band of 0.75 to 2.5 Hz corresponding to a general heart rate band of 45 to 150 BPM in order to remove noise other than heart rate components.

The facial fine motion signal extraction may include a dimensionality reduction step of extracting a final facial fine motion signal by removing an interaction factor that a heartbeat component gives to each RGB (red, green, blue) color through independent component analysis (ICA).

In the present disclosure, the mental state classification method 100 may further include a calibration step. The calibration step may be performed, by the mental state classification server 200, by receiving the facial image from the computing device 300 in real time before the step of providing the display 12 with a questionnaire for classifying the mental state (S150). The calibration step, as described in the step of controlling to extract the heart rate variability data (S160), may be similar to the method of extracting a face fine motion signal from the described face image, normalizing each fine motion signal to remove noise other than heartbeat components from the extracted face fine motion signal, and applying a band-pass filter for heart rate bands. However, the method is not necessarily limited to performing calibration by the mental state classification server 200. The mental state classification method of the present disclosure may self-calibrate a face image generated by taking a picture in the computing device 300 by an arithmetic processing unit included in the computing device 300.

The mental state classification method 100 may further include, after controlling to extract heart rate variability data (S160), classifying at least one mental state of the user by analyzing the extracted heart rate variability. The at least one mental state of the user is at least one of psychological condition is at least one of major depression disorder, anxiety disorder, adjustment disorder, PTSD, suicidal ideation, and insomnia.

The step of extracting the heart rate variability data of the mental state classification method 100 of the present disclosure may further include a step of, by the mental state classification server 200, extracting heart rate variability (HRV) data by performing image processing on the received image in real time. For example, the method of extracting the HRV data may include steps of, receiving, by the mental state classification server 200, an image from the computing device 300 in real time and detecting a user's face in a frame of the received image; defining a measurement region in the detected face; tracking a head movement by a fine movement and extracting a color-based fine movement signal by extracting a corresponding fine change in color; converting the extracted facial motion signal into a frequency band through fast Fourier transform (FFT) to extract a power spectrum and normalize it to extract a relative frequency; selecting K heartbeat candidates by comparing a similarity between a relative frequency of the facial motion signal extracted from the image and a constructed rule base; recognizing an average heart rate of the K heart rate candidate groups extracted from the rule base based on the K-nearest neighbor algorithm through similarity comparison as a final heart rate; and extracting an HRV variable (HRV data) by calculating the HRV variable from the final recognized heartbeat using an HRV formula. Examples of the HRV variables are shown in Table 2 below. In addition, in the step of extracting the color-based fine motion, each fine motion signal may be normalized and a bandpass filter for a heartbeat band may be applied to remove noise other than the heartbeat component. For example, in the step of defining the measurement region in the detected face, the measurement region may be set to include a middle of a forehead and both cheeks of the user's face.

TABLE 2

<Descriptions of the HRV variables>

| No. | Domain | HRV variable | Explanation |
|---|---|---|---|
| 1 | Time Domain | HR | Average heart rate per minute (bpm) |
| 2 |  | SDNN | Standard deviation of intervals between all peaks |
| 3 |  | RMSSD | Square root of the mean of the sum of the squares of the differences between adjacent peaks |
| 4 |  | pNN50 | Proportion (%) of difference between adjacent peaks greater than 50 msec. |
| 5 | Frequency Domain | VLF | Power values in the 0.0033 to 0.04 Hz band in the frequency domain |
| 6 |  | LF | Power values in the 0.04 to 0.15 Hz band in the frequency domain |
| 7 |  | HF | Power values in the 0.15-0.4 Hz band in the frequency domain |
| 8 |  | VLF (%) | VLF divided by the total power value (power value in the 0.0033~0.4 Hz band) |
| 9 |  | LF (%) | LF divided by total power value (power value in 0.0033~0.4 Hz band) |
| 10 |  | HF (%) | HF divided by the total power value (power value in the 0.0033~0.4 Hz band) |
| 11 |  | lnVLF | VLF taken as natural logarithm |
| 12 |  | lnLF | LF taken as natural logarithm |
| 13 |  | lnHF | HF taken natural logarithm |
| 14 |  | LF/HF | LF divided by HF |
| 15 |  | VLF/HF | VLF divided by HF |
| 16 |  | Total Power | Power spectrum band between 0.0033 and 0.4 Hz |
| 17 |  | Dominant Power | The power value of the highest peak in the power spectrum |
| 18 |  | Dominant Hz | Frequency value (Hz) of the highest peak in the power spectrum |
| 19 |  | Peak power | Power spectrum band from −0.015 Hz to +0.015 Hz centered at peak Hz |
| 20 |  | Peak Hz | Frequency value (Hz) of the highest peak in the power spectrum band between 0.04 and 0.26 Hz |
| 21 |  | Coherence ratio | Peak Power divided by the difference between Total Power and Peak Power |

Therefore, according to this configuration, in the mental state classification method 100 of the present disclosure, since the user can take the questionnaire and the user's face in a stable state in the surrounding noise, ambient brightness, and the position of the face captured by the camera 14 within an appropriate range that can create an environment in which the heart rate variability can be measured normally, a highly accurate heart rate variability close to the user's actual heart rate variability can be extracted.

For example, the mental state may be at least one of major depressive disorder, anxiety disorder, adjustment disorder, PTSD, suicidal ideation, and insomnia. For example, the mental state classification method 100 may classify a probability that the mental state of the user is major depressive disorder as a score (L) or severity (S).

In one embodiment, the probability may be expressed as a percentage (not shown) or a range of scores (L). The severity (S) of the mental health condition may be represented by classifying a scale into mild, moderate, and severe, for example. Alternatively, the severity (S) of the mental health condition may be represented by classifying a scale into five stages of, for example, no disability, mild, medium, slightly severe, and severe. This classification of stages is only an example, and such stages can be variously modified by setting.

On the other hand, the mental state classification method 100 of the present disclosure, by the processor 18, in response to each of the ambient noise of the user, the ambient brightness of the user's face obtained from the image F generated by photographing with the camera 14, and the location of the user's face obtained from the image F being checked as not suitable for the heart rate variability measurement environment, may be configured to classify the generated image F as unreliable data.

Referring to FIG. 5 to FIG. 8, the step of controlling the camera 14 to extract heart rate variability data from an image F generated by photographing the user's face while the user inputs an answer to the questionnaire in the mental state classification method 100 may include steps of, by the processor 18, controlling to display a noise suitable image A1 or a noise unsuitable image A2 indicating whether the ambient noise is suitable or unsuitable on the display 12 according to whether the ambient noise is suitable for the heart rate variability measurement environment; by the processor 18, controlling to display a brightness suitable image B1 or a brightness unsuitable image B2 indicating whether the ambient brightness is suitable or unsuitable on the display 12 according to whether the ambient brightness is suitable for the heart rate variability measurement environment; and, by the processor 18, controlling to display a face position suitable image C1 or face position unsuitable image C2 indicating whether the face position is suitable or unsuitable on the display 12 according to whether the face position is suitable for the heart rate variability measurement environment.

Therefore, according to this configuration, the mental state classification method 100 of the present disclosure can maintain ambient noise, ambient brightness, and the position of the face captured by the camera 14 within an appropriate range to create an environment in which heart rate variability can be normally measured even while the user is conducting a questionnaire, so that it is possible to effectively reduce errors in measuring heart rate variability that may occur during the questionnaire, which is advantageous as it not only can extract heart rate variability with high accuracy close to the actual heart rate variability of the user, but also classify the user's psychology with high reliability based on the user's answer and the extracted heart rate variability.

Meanwhile, referring to FIG. 6 to FIG. 8 together with FIG. 3, the step of controlling to display images indicating whether the heart rate variability measurement environment is suitable for display on the display 12, may further include a step of displaying, by the processor 18, a notification text on the display 12 according to whether each of the ambient noise, the ambient brightness, and the face position is suitable for the heart rate variability measurement environment.

For example, as shown in FIG. 6, the step of controlling the display of images indicating whether the heart rate variability measurement environment is suitable for displaying on the display 12, in response to the ambient noise not falling within a range suitable for the heart rate variability measurement environment, may include controlling, by the processor 18, to display a notification text T1 "it's little noisy around!" as a pop-up window on the display 12.

For example, as shown in FIG. 7, the step of controlling the display of images indicating whether the heart rate variability measurement environment is suitable for displaying on the display 12, in response to the ambient brightness not falling within a range suitable for the heart rate variability measurement environment, may include controlling, by the processor 18, to display a notification text T2 "please check the brightness of the lighting!", "use the smartphone light sensor to adjust the ambient brightness", "you are in a very dark place. please move to another place", or "you are in a place that is too bright right now. please move to another place" as a pop-up window on the display 12.

For example, as shown in FIG. 8, the step of controlling the display 12 to display images indicating whether or not the heart rate variability measurement environment is suitable (S140), if the location of the user's face photographed by the camera 14 before and during the questionnaire is not within a range suitable for the heart rate variability measurement environment, may include controlling, by the processor 18, to display a notification text T3 "I can't see your face well!" as a pop-up window on the display 12.

Meanwhile, the mental state classification method 100 of the present disclosure may further include a step of controlling to, before and during the questionnaire on the user's mental state, by the processor 18, to display a notification content (not shown) on the display 12 leading the camera 14 to be positioned above the display 12. For example, the notification content leading the camera 14 to be positioned above the display 12 may be "please set the screen mode to portrait mode", "please rotate the device so that the camera is positioned above the screen", etc.

On the other hand, the mental state classification method 100 of the present disclosure may further include steps of: checking a degree of shaking of the face of the image F photographed by the camera 14; and, in response to the shaking of the camera 14 not being within a range suitable for the heart rate variability measurement environment, controlling to display notification content (not shown) on display 12 inducing the user to stably fix the camera 14 so as to minimize shaking of the camera 14. For example, the notification content leading the user to stably fixate the camera 14 may be "please start by holding the smartphone stably with both hands".

Meanwhile, the mental state classification method 100 of the present disclosure may further include steps of: based on the state in which the face photographed by the camera 14 looks at the camera 14 from the front, checking whether the angle of inclination of the face to the roll axis is within a range of ±15 degrees, the angle of inclination of the face to the yaw axis is within a range of ±20 degrees, and the angle of inclination of the face to the pitch axis is within a range of ±10 degrees; and, in response to the angles not being within a range suitable for the heart rate variability measurement environment, by the processor 18, controlling to display on the display 12 a notification content that leads the user to bring the angles within the range. For example, the notification content that leads the user to bring the angle of inclination of the face to the roll axis is within a range of ±15 degrees, the angle of inclination of the face to the yaw axis is within a range of ±20 degrees, and the angle of inclination of the face to the pitch axis is within a range of ±10 degrees may be "you must stare at the screen straight."

On the other hand, the mental state classification method 100 of the present disclosure may further include steps of: by the processor 18, checking the distance between the camera 14 and the user's face; and, in response to the distance not falling within the range suitable for the heart rate variability measurement environment, by the processor 18, before and during the questionnaire on the mental state of the user computing device 300, controlling to display notification content on the display 12 that leads the position of the user's face to come within a distance range of 0.5 to 1 meter from the camera 14. For example, the notification content may be "Please gaze the camera within a distance of 1 m."

Meanwhile, the mental state classification method 100 of the present disclosure may further include steps of: checking whether a background around the user's face is a single color background with few patterns or shapes by the processor 18; and, in response to the background not falling within a range suitable for the heart rate variability measurement environment, by the processor 18, before and during the questionnaire on the mental state of the user computing device 300, controlling to display on the display 12 of notification content that leads the user, so that the background around the face of the user captured by the camera 14 of the user computing device 300 to be a single color background with few patterns or shapes.

Therefore, according to this configuration, the mental state classification method 100 of the present disclosure can extract a highly accurate heart rate variability close to the actual heart rate variability of the user, as it can help the user to well recognize situations in which each of the ambient noise, ambient brightness, and the position of the face captured by the camera 14 that are suitable for an environment in which heart rate variability can be measured normally is not suitable, making it possible to effectively reduce errors in measuring heart rate variability that may occur during the questionnaire.

Meanwhile, referring to FIG. 6 again, the step of providing a questionnaire for classifying a mental state to the display 12 (S150) may further include a step of, by the processor, controlling to display an image of the user's face including at least a middle of a forehead and both cheeks on the display 12 while conducting a questionnaire on the user's mental state.

Here, the face image captured by the camera 14 may be displayed on the top of a chat (i.e., conversation) screen with a virtual person (i.e., agent) for classifying a mental state. The face image may represent the middle of the forehead and both cheeks of the user's face. In this regard, according to the Objective Self-Awareness (OSA) theory and a method proven in OSA theory-related experiments, by displaying the minimum camera 14 view area in which the user's face is photographed on the display 12, the camera 14 can serve as a mirror, so that the user recognizing his or her own appearance can evoke self-reflection and inputs more truthful answers.

In one embodiment, the display 12 may show the middle of the forehead and both cheeks of the user's face and may not show the mouth. Even when the display 12 shows only the middle of the forehead, both cheeks, and surrounding areas of the user's face, heart rate variability measurement may be performed using an entire face image or an area other than the middle of the forehead and both cheeks of the user's face.

Therefore, the mental state classification method 100 of the present disclosure can evoke self-reflection on the user who has recognized his/her appearance, thus the user may input truthful answers to the questionnaire while the user inputs an answer to the questionnaire through the display 12 of the user computing device 300.

On the other hand, the step of providing a questionnaire for classifying the mental state (S150), may further include steps of: by the processor 18, generating time information by measuring a time from when the question of the questionnaire is provided on the display 12 to when the user's answer to the question is input through the display 12; and controlling, by the processor 18, the display 12 to display an inverted question for checking whether the user consistently answered during the questionnaire.

Here, the "reverse question" refers to a question asked in reverse in a questionnaire item (for example, a question for which a response is the opposite of an existing question). As in FIG. 6, if the "main question" consists of "Did you lose interest in or did you feel no pleasure in your usual work?", the "reverse question" may consist of "Did you find interest or enjoyment in your usual work?".

In general, a reverse question is used to confirm a reliability of the answer, such as whether the user consistently gave honest answers to questions in the questionnaire or mechanically selected one answer in the questionnaire.

In addition, the mental state classification method 100 of the present disclosure, after the step of controlling to extract the heart rate variability data, may further include, by the processor 18, a step of determining whether the user's answer to the questionnaire is an insincere answer based on at least one of the time information and the ratio of consistent answers to the inverse question.

For example, the step of determining whether an answer is insincere may classify the answer as insincere when the time taken is less than 20 milliseconds (ms) on average, from the time when the question of the questionnaire is provided to the display 12 to the time when the user's answer to the question is input through the display 12.

For example, the step of determining whether the answer is insincere may further include a step of, by the processor 18, classifying the user's answer as an insincere answer when the ratio of the user's answer to the inverse question of the questionnaire that is consistent with the user's answer to the main question is less than or equal to a predetermined value. For example, the step of determining whether the answer is insincere may determine, by the processor 18, that the answer to the user's questionnaire, in which the rate of the user's answer to the inverse question of the questionnaire that is consistent with the user's answer to the main question of the questionnaire is 60% or less, as an insincere answer.

Further, the mental state classification method 100 of the present disclosure, may further include steps of: by the processor 18, tracking pupils of the user to obtain time information at which the user gazes at a question of the questionnaire; and, by the processor 18, determining an answer of the user, in which a time that the user's gaze deviates from the question of the questionnaire displayed on the display 12 is more than a predetermined time or a time that the user's gaze stays on the question of the questionnaire is less than the predetermined time, as an insincere answer.

Therefore, the mental state classification method 100 is advantageous in that, as it is possible to check whether the user's answer is insincere, the user's psychology can be classified with high reliability based on the user's answer and the extracted heart rate variability.

In addition, the mental state classification method 100 of the present disclosure, may further include a step of, by the processor 18, determining the mental state of the user by displaying a negative picture showing the face of a person expressing emotions such as anger, fear, and sadness and a happy picture showing a face with a happy expression sequentially on the display 12 while the user's questionnaire is in progress and then measuring a time of gazing of the user at each of the negative and happy photos shown in the generated image by photographing the user's face with the camera 14. For reference, a patient suspected of depression will spend a longer time gazing at the negative photo than a normal person and spend less time gazing at a photo containing than happy expression than a normal person.

In one embodiment, the mental state classification method 100 of the present disclosure can measure a time that the user spent gazing at each of the negative and happy photos of the user and determine the user's answer as an insincere answer when the user's gazing time at the negative photo is relatively longer than that of a normal person.

Figure 9:
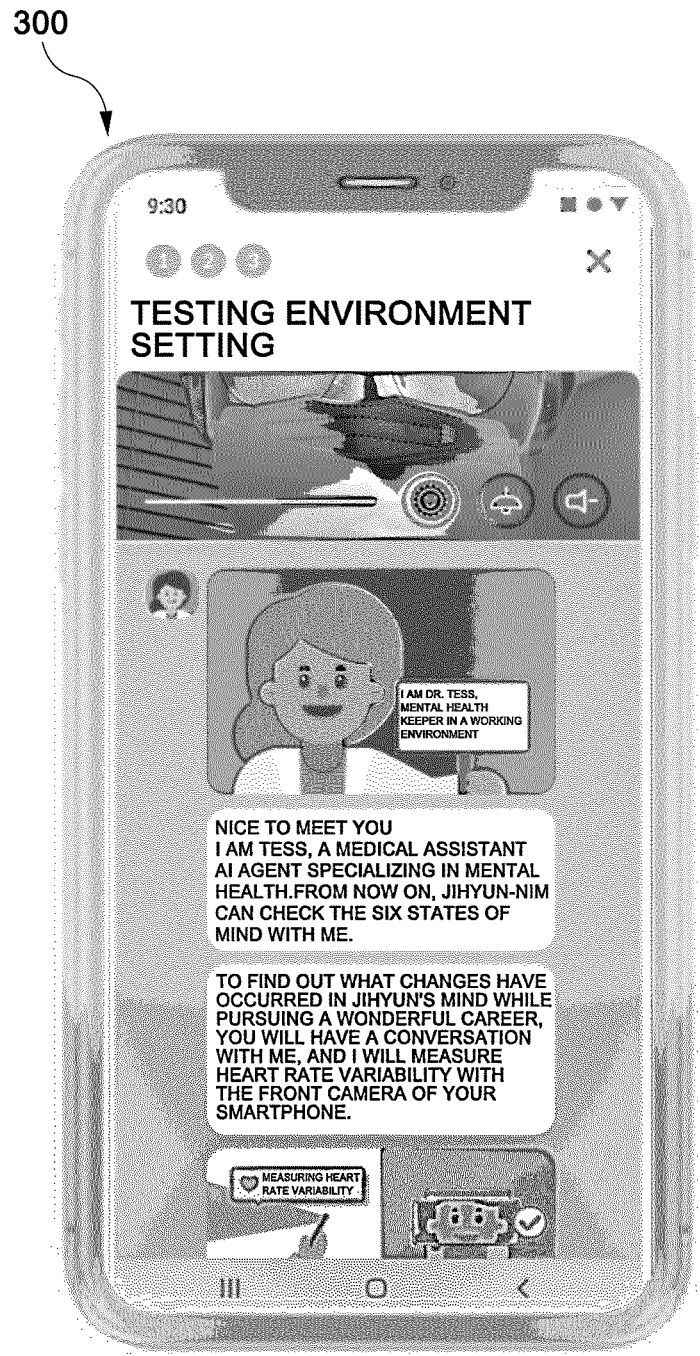
FIG. 9 is a diagram illustrating a state in which notification contents for inducing a user to retake a questionnaire are displayed on a computing device according to an embodiment of the present disclosure.

FIG. 9 is a diagram illustrating a state in which notification content for leading the user to retake a questionnaire is displayed on the computing device 300 according to an embodiment of the present disclosure.

Referring to FIG. 9, in the mental state classification method 100 of the present disclosure, after the step of determining whether the answer to the user's questionnaire is an insincere answer, may perform, by the processor 18, in response to the user's answer to the questionnaire determined to be insincere, a step of displaying on the display 12 an item for confirming a reliability of the user's answer to the questionnaire to the user.

In addition, the mental state classification method 100 of the present disclosure, after the step of displaying a question for confirming the reliability of the user's answer to the questionnaire to the user, in response to the user inputting an answer that his or her answer to the questionnaire is not highly reliable, may perform, by the processor 18, a step of controlling the display 12 to display notification content that leads the user to retake the questionnaire.

Accordingly, the mental state classification method 100 of the present disclosure is advantageous in that the user's psychology can be classified with higher reliability based on the user's answer and the extracted heart rate variability, by leading the user to retake the questionnaire in response to the user's answer being judged to be insincere.

On the other hand, the mental state classification method 100 of the present disclosure, after the step of extracting the heart rate variability data, by the mental state classification server 200, may perform a step of executing a first algorithm to obtain a first numerical value representing a probability that the user is in the mental state based on an answer to the questionnaire input by the user. The first numerical value may include a scale representing the severity of the user's mental health condition. In one embodiment, the probability may be expressed as a percentage or a range of scores. The severity of the mental health condition may be represented by classifying a scale into, for example, mild, moderate, and severe. Alternatively, the severity of the mental health condition may be represented by classifying a scale into five stages of, for example, no disability, mild, moderate, slightly severe, and severe. This classification of stages is only an example, and such stages can be variously modified by setting.

Figure 10:
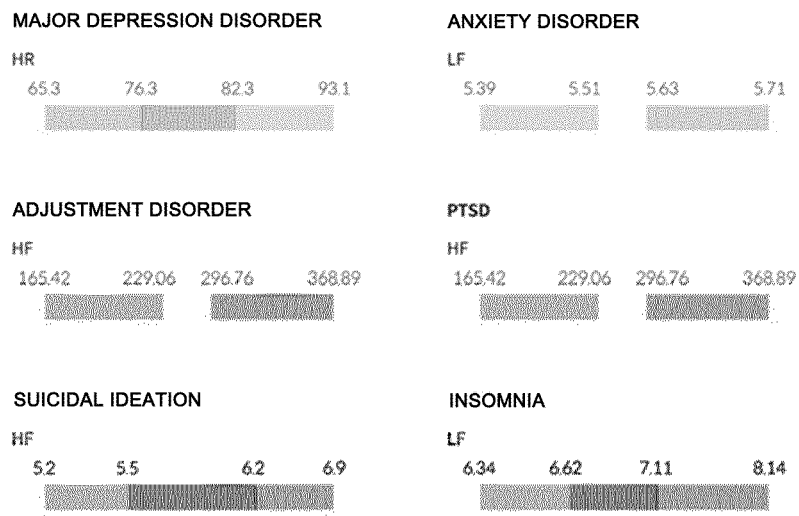
FIG. 10 shows classification reference graphs for categorizing a plurality of mental states through heart rate variability data of a mental state classification server according to an embodiment of the present disclosure.

FIG. 10 shows classification reference graphs for discriminating a plurality of mental states through heart rate variability data of a mental state classification server according to an embodiment of the present disclosure.

Referring to FIG. 10, the mental state classification method 100 of the present disclosure, after the step of extracting the heart rate variability data, may perform, by the mental state classification server 200, a step of obtaining a second numerical value representing a probability that the user corresponds to a mental state based on the heart rate variability data of the user extracted by executing the second algorithm. Here, the second numerical value may represent the severity of the user's mental state. For example, after the mental state classification server 200 extracts HRV variables (HRV data) such as HR value, LF value, and HF value by real-time image processing of the received image, the mental state of the user may be classified by analyzing the extracted HR value, LF value, and HF value as cutoff criteria of a mental disorder screening model. Here, the HR value is related to symptoms of depression, the LF value is related to mental stress and fatigue, and the HF value may decrease when one is suffering from continuous stress, fear, anxiety, or worry.

For example, based on the graph shown in FIG. 10, by the mental state classification server 200, major depressive disorder may be classified as 'not depressive' when the HR value was 65.3 to less than 76.3, 'moderate' when the HR value was 76.3 to 82.3, and 'severe' when the HR value was greater than 82.3 to 93.1.

For example, based on the graph shown in FIG. 10, by the mental state classification server 200, the anxiety disorder may be classified as 'not anxious' when the LF value is 5.63 to 5.71, and classified as 'severe' when the LF value is 5.39 to 5.51.

For example, based on the graph shown in FIG. 10, by the mental state classification server 200, the adjustment disorder may be classified as 'no adjustment disorder' when the HF value is 296.76 to 368.89, and classified as 'severe' when the HF value is 165.42 to 229.06.

For example, based on the graph shown in FIG. 10, by the mental state classification server 200, the post-traumatic stress disorder (PTSD) can be classified as 'not PTSD' when the HF value is 296.76 to 368.89, and classified as 'severe' when the HF value is 165.42 to 229.06.

For example, based on the graph shown in FIG. 10, by the mental state classification server 200, the possibility of suicidal ideation may be classified as 'not suicidal risk' when the HF value is less than 6.2 to 6.9, classified as 'slight' when the HF value is 5.5 to 6.2, and 'severe' when the HF value is less than 5.2 to 5.5.

For example, based on the graph shown in FIG. 10, by the mental state classification server 200, the insomnia may be classified as 'not insomnia' when the LF value is greater than 7.11 to 8.14, classified as 'slight' when the LF value is 6.62 to 7.11, and classified as 'severe' when the LF value is less than 6.34 to 6.62.

Moreover, the mental state classification method 100 of the present disclosure, after obtaining the first numerical value and obtaining the second numerical value, may further include, by the mental state classification server 200, a step of executing a third algorithm and obtaining a third numerical value representing a probability that the user corresponds to a mental state based on the first numerical value and the second numerical value.

Here, the third numerical value may include the severity of the user's mental state. In one embodiment, the third algorithm may set weights for each of the first and second numerical values and obtain the third values based on the weights. For example, the mental state classification server 200, by executing the third algorithm, may derive the third numerical value representing a final classification result by reflecting the mental state result classified according to the first numerical value by 95% in the final classification result and reflecting the mental state result classified according to the second numerical value by 5%. The step of obtaining the third numerical value of the mental state classification method 100 of the present disclosure, by the mental state classification server 200, may further include the step of executing the third algorithm to derive the third numerical value representing the final classification result by multiplying a weight by the second numerical value to the first numerical value.

Figure 11:
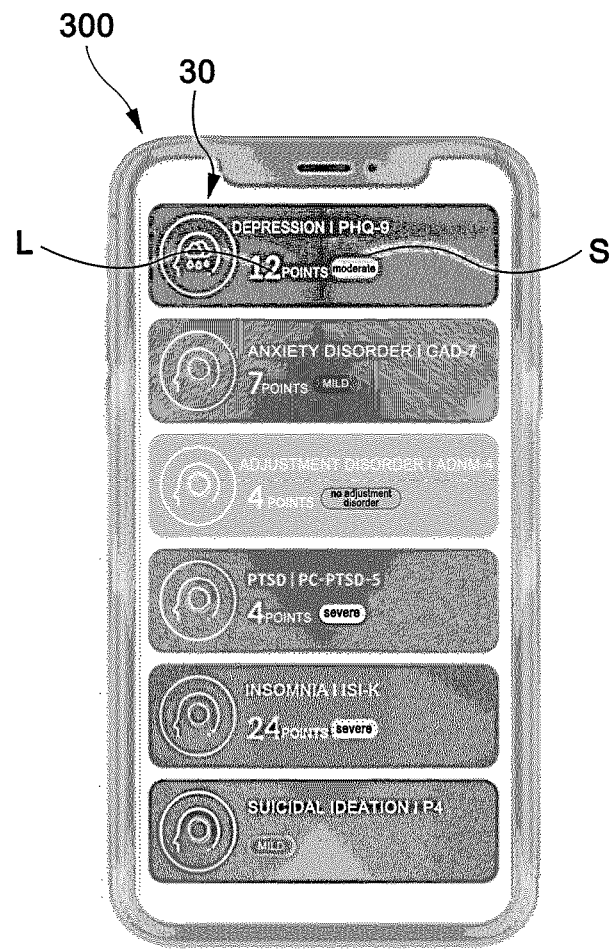
FIG. 11 is a diagram illustrating a state in which a mental state classification result report is provided to a computing device according to an embodiment of the present disclosure.

FIG. 11 is a diagram showing a mental state classification result report provided to the computing device 300 according to an embodiment of the present disclosure.

Referring to FIG. 11, the mental state classification method 100, by the mental state classification server 200, may further include a step of generating a mental state classification result report 30 indicating the third numerical value of the mental state, and transmitting the generated mental state classification result report 30 to the computing device 300.

In the mental state classification result report 30, the probability that the user corresponds to at least one mental state may be expressed as a percentage and a severity. For example, it may include five levels of no severity, mild, moderate, moderately severe, and severe, four levels of no severity, mild, moderate, and severe, or three levels of no severity, moderate, and severe. This classification is an example, and the classification may be two levels or six levels or more.

Meanwhile, again referring to FIG. 6 together with FIG. 1 and FIG. 2, the present application may provide a mental state classification server 200 according to an embodiment of the present disclosure. The mental state classification server 200 may be configured to classify the user's mental state through the user computing device 300.

The mental state classification server 200 includes a computing system, hardware running programs, software running on the hardware, and cloud services. The mental state classification server 200 may be connected to the computing device 300 or other servers through a network. In addition, the mental state classification server 200 may include hardware such as a processor, a storage or database, and a communication module. Further, the mental state classification server 200 may receive personal information of the user from the computing device 300 and store it. To this end, the mental state classification server 200 may have a database (not shown) to store personal information. However, it is not limited thereto, and the mental state classification server 200 may transmit the user's personal information to an external server (e.g., a cloud server) to store the user's personal information.

Personal information may be stored in a storage space of an external server accessible to the mental state classification server 200. Here, 'personal information' may be biographical information of the user. For example, the personal information may be at least one of real name, gender, age (date of birth), phone number, and workplace information (company name, department, team, job title, number of years of service).

The mental state classification server 200 may be configured to: receive sound information detected by the user computing device 300; receive an image F generated by being photographed by the user computing device 300, based on the received sound information and the received image F; check whether each of the user's ambient noise, the ambient brightness from the image F, and the user's face position in the image F is suitable for a heart rate variability measurement environment; transmits a first control signal for controlling the user computing device 300 to the user computing device 300 based on a result of checking whether the heart rate variability measurement environment is suitable, wherein the first control signal is a control signal so that the user computing device 300 to display images F indicating whether each of the ambient noise, the ambient brightness, and the face position are suitable for the heart rate variability measurement environment on the display 12 of the user computing device 300; in response to checking that each of the ambient noise, the ambient brightness, and the face position is suitable for the heart rate variability measurement environment, transmit a second control signal for controlling the user computing device 300 to the user computing device 300 so that a questionnaire for mental state classification is displayed on the display 12; receive an image F generated by photographing the user's face from the user computing device 300 while the user inputs an answer to the questionnaire through the user computing device 300; and extract heart rate variability data from answers to the questionnaire and the received image F.

Therefore, according to this configuration, the mental state classification server 200 of the present disclosure, as it can provide questionnaire and photograph the user's face in a stable state in a suitable range of ambient noise, ambient brightness, and the position of the face captured by the camera 14 that can create an environment in which heart rate variability can be measured normally, is advantageous in that heart rate variability, which is close to the actual heart rate variability of the user, can be extracted with high accuracy, and the user's mental state can be classified with high reliability based on the user's answer and the extracted heart rate variability.

Meanwhile, referring to FIG. 6 to FIG. 8, the mental state classification server 200, based on the result of checking whether the heart rate variability is suitable for the measurement environment, may transmit a 1-1 control signal to the user computing device 300 to display a suitable noise image A1 or an unsuitable noise image A2 indicating whether the ambient noise is suitable or unsuitable on the display 12.

The mental state classification server 200, may transmit a 1-2 control signal to the user computing device 300 to display a suitable brightness image B1 or an unsuitable brightness image B2 indicating whether the ambient brightness is suitable or unsuitable on the display 12.

The mental state classification server 200, may transmit a 1-3 control signal to the user computing device 300 to display a suitable face position image C1 or an unsuitable face position image C2 indicating whether the face position is suitable or unsuitable on the display 12.

Therefore, according to this configuration, the mental state classification server 200 of the present disclosure, since it can maintain ambient noise, ambient brightness, and the position of the face photographed by the camera 14 in an appropriate range that can create an environment in which heart rate variability can be normally measured even while the user is conducting a questionnaire, is advantageous as it not only can extract heart rate variability with high accuracy close to the actual heart rate variability of the user, but also can classify the user's mental state with high reliability based on the user's answer and the extracted heart rate variability, for it can effectively reduce errors in measuring heart rate variability that may occur during the questionnaire.

In addition, the mental state classification server 200, may transmit a third control signal to the user computing device to display a notification text indicating whether each of the ambient noise, the ambient brightness, and the face position is suitable for the heart rate variability measurement environment on the display 12, based on a result of checking whether the heart rate variability measurement environment is suitable while providing a questionnaire for classifying a mental state.

For example, as shown in FIG. 6, the mental state classification server 200, in response to determining that the ambient noise does not come within a range suitable for the heart rate variability measurement environment, the display 12 of the user's computing device 300 may be controlled to display a notification text T1 "it's little noisy!" as a pop-up window.

For example, as shown in FIG. 7, the mental state classification server 200, in response to determining that the ambient brightness does not come within a range suitable for the heart rate variability measurement environment, may control the display 12 of the user's computing device 300 to display a notification text T2 "please check the brightness of the lighting!" as a pop-up window.

For example, as shown in FIG. 8, the mental state classification server 200, in response to determining that the face position does not come within a range suitable for the heart rate variability measurement environment, may control the display 12 of the user's computing device 300 to display a notification text T3 "I can't see your face well!" as a pop-up window.

Therefore, according to this configuration, the mental state classification server 200 of the present disclosure, as it can assist the user to notice a situation where the ambient noise, ambient brightness, and the position of the face photographed by the camera 14 are not suitable for the environment in which heart rate variability can be measured normally while the user is conducting a questionnaire, can effectively reduce errors in measurement of heart rate variability that may occur during the questionnaire, and thus extract heart rate variability with high reliability close to the actual heart rate variability of the user.

On the other hand, the mental state classification server 200 of the present disclosure, by performing machine learning of artificial intelligence, based on the mental state classification result data of the plurality of users and the result data of the medical examination of the plurality of users by a person (e.g., specialist), may be configured to derive an analysis algorithm capable of more precise measurement, by analyzing an influence of error in the mental classification result according to at least one of the plurality of ambient brightness (illuminance) captured by cameras 14 of the user, direction (angle) in which the user's face gazes at the camera 14, face size according to the photographing distance of the face, and a color difference value between a surrounding background of the face and the face.

Referring FIG. 1 in conjunction with FIG. 11, the mental state classification server 200, may be configured to generate a mental state classification result report 30 indicating the mental state having the third numerical value. In addition, the mental state classification server 200 may indicate the probability that the user corresponds to at least one mental state in the mental state classification result report 30 as a percentage and a severity level. For example, it may include five levels of no severity, mild, moderate, moderately severe, and severe, four levels of no severity, mild, moderate, and severe, or three levels of no severity, moderate, and severe. This classification is an example, and the classification may be two levels or six levels or more.

For example, the major depressive disorder may be classified into five levels: no depression, mild, moderate, moderately severe, and severe. For example, the anxiety disorder can be divided into four levels: no anxiety, mild, moderate, and severe. For example, the adjustment disorder may be divided into two levels: no adjustment disorder and severe. For example, PTSD can be divided into three levels: no PTSD, moderate, and severe. For example, the insomnia may be divided into four levels: no insomnia, mild, slightly severe, and severe. For example, the suicidal ideation may be classified into three levels: no suicidal risk, mild, and severe. It will be understood that the above classification of stages for each mental state is exemplary, and the classification of stages may be different according to settings.

Therefore, according to this configuration, the mental state classification server 200 according to an embodiment of the present disclosure, considering both the results of classifying the mental state based on the answers to the questionnaire for classifying the mental state and the result of classifying the mental state based on the heart rate variability data, can finally classify the mental state of the user. Accordingly, the mental state classification server 200 of the present disclosure can effectively increase the accuracy and reliability of the mental state classification of the user.

Meanwhile, the present application may provide a computing device 300 according to an embodiment of the present disclosure. Referring to FIG. 6 together with FIG. 1 and FIG. 2, the computing device 300 for classifying the mental state of a user according to an embodiment of the present disclosure includes a microphone 11, a camera 14, and a display 12, and a processor 18.

Specifically, the microphone 11 is configured to detect ambient noise of the user. The camera 14 is configured to photograph the user's face to create an image F. The processor 18 is configured to check whether each of the ambient noise detected by the microphone 11, the ambient brightness obtained from the image F, and the face position obtained from the image are suitable for the heart rate variability measurement environment.

Here, the computing device 300, by the processor 18, after digitizing the analog signal of the ambient noise detected by the microphone 11, may analyze the ambient noise from the digitized signal data to measure the level of the ambient noise, and may check whether the measured loudness of ambient noise is suitable for the heart rate variability measurement environment.

In addition, the computing device 300, after analyzing the image F generated by photographing by the camera 14 using an image analysis module stored in the computing device 300, may determine whether the ambient brightness and the position of the user's face are suitable for the heart rate variability measurement environment through the analyzed result.

Further, the processor 18 is configured to control the display 12 to display images indicating whether each of the user's ambient noise, ambient brightness, and face position is suitable for a heart rate variability measurement environment.

Further, the processor 18 is configured, in response to checking that each of the ambient noise, the ambient brightness, and the face position is suitable for the heart rate variability measurement environment, to control display 12 to display a questionnaire for classifying the mental state of the user. And the processor 18 is configured to extract heart rate variability data from an image F generated by photographing the user's face by the camera 14 while the user inputs an answer to the questionnaire.

Therefore, according to this configuration, the computing device 300 of the present disclosure, because it can provide questionnaire and photograph the user's face in a stable state in a suitable range of ambient noise, ambient brightness, and the position of the face captured by the camera 14 that can create an environment in which heart rate variability can be normally measured, can not only extract heart rate variability with high accuracy close to the actual heart rate variability of the user, but also is advantageous in that the user's mental state can be classified with high reliability based on the user's answer and the extracted heart rate variability.

Meanwhile, referring to FIG. 6 to FIG. 8, the processor 18 may control the display 12 to display, based on the result of checking whether the heart rate variability is suitable for the measurement environment, a noise conforming image A1 or a noise unsuitable image A2 indicating whether the ambient noise is suitable or unsuitable, a brightness suitable image B1 or a brightness unsuitable image B2 indicating whether the ambient brightness is suitable or unsuitable, and a face position suitable image C1 or a face position inappropriate image C2 indicating whether the face position is suitable or unsuitable.

Therefore, according to this configuration, the mental state classification server 200 of the present disclosure, since it is possible to maintain the ambient noise, ambient brightness, and the position of the face captured by the camera 14 in an appropriate range that can create an environment in which the heart rate variability can be normally measured even while conducting the questionnaire, may effectively reduce errors in measuring heart rate variability that may occur during the questionnaire, and is advantageous in that heart rate variability, which is close to the actual heart rate variability of the user, can be extracted with high accuracy and the user's mental state can be classified with high reliability based on the user's answer and the extracted heart rate variability.

In addition, the processor 18, based on the result of checking whether the heart rate variability is suitable for the measurement environment, may control the display 12 to display a notification text indicating whether each of the ambient noise, the ambient brightness, and the face position is suitable for the heart rate variability measurement environment.

For example, as shown in FIG. 6, the processor 18, when the ambient noise does not fall within a range suitable for the heart rate variability measurement environment, may control the display 12 to display a notification text T1 "it's little noisy!" as a pop-up window.

For example, as shown in FIG. 7, the processor 18, when the ambient brightness does not come within a range suitable for the heart rate variability measurement environment, may control the display 12 to display a notification text T2 "please check the lighting brightness!" as a pop-up window.

For example, as shown in FIG. 8, the processor 18, when the position of the face does not come within a range suitable for the heart rate variability measurement environment, may control the display 12 to display a notification text T3 "I can't see your face well!" as a pop-up window.

Therefore, according to this configuration, the computing device 300 of the present disclosure, as it can assist the user to recognize a situation in which the ambient noise, ambient brightness, and the position of the face photographed by the camera 14 are not suitable for the environment in which the heart rate variability can be measured normally while the user is conducting the questionnaire, it can effectively reduce errors in measuring heart rate variability that may occur during the questionnaire, and it not only can extract heart rate variability with high accuracy close to the actual heart rate variability of the user, but also is advantageous in that the user's mental state can be classified with high reliability based on the user's answer and the extracted heart rate variability.

Meanwhile, referring to FIG. 2 and FIG. 7, the processor 18 may control the display 12 to display the progress rate of the heart rate variability measurement as a graph (G) or numerical value (P) while conducting a questionnaire on the user's mental state. For example, as shown in FIG. 7, the progress rate of the heart rate variability measurement may be displayed on the display 12 as a graph (G) in the form of a progress bar and a percentage value (P). Therefore, the computing device 300 of the present disclosure, by this configuration, as it can assist the user to recognize the progress of camera shooting for measuring heart rate variability while inputting an answer to the questionnaire, makes it possible to secure a sufficient amount of user's face images, facilitating the extraction of the heart rate variability.

In the embodiments disclosed herein, the arrangement of the illustrated components may vary depending on the environment or requirements in which the invention is implemented. For example, some components may be omitted or some components may be integrated and implemented as one.

In addition, the arrangement order and connection order of some components may be changed.

Although the above has shown and described various embodiments of the present disclosure, the present disclosure is not limited to the specific embodiments described above. The above-described embodiments can be variously modified and implemented by those skilled in the art to which the present invention pertains without departing from the gist of the present disclosure claimed in the appended claims and these modified embodiments should not be understood separately from the technical spirit or scope of the present disclosure. Therefore, the technical scope of the present disclosure should be defined only by the appended claims.

The described embodiments of the present disclosure also allow certain tasks to be performed on a distributing computing environment performed by remote processing devices that are linked through a communications network. In the distributed computing environment, program modules may be located in both local and remote memory storage devices.

In the embodiments disclosed herein, the arrangement of the illustrated components may vary depending on the environment or requirements in which the invention is implemented. For example, some components may be omitted or some components may be integrated and implemented as one.

What is claimed is:

1. A method of classifying a mental state of a user using a computing device, which includes a microphone, a camera, a display, a wireless communication unit, and a processor, and a mental state classification server, comprising:
   by the microphone, detecting ambient noise of the user;
   by the camera, generating an image by photographing a face of the user;
   by the processor, checking whether each of ambient noise of the user, ambient brightness of the face of the user obtained from the image, and a face position of the user obtained from the image is suitable for a heart rate variability measurement environment;
   by the processor, controlling to display on the display images indicating whether each of the ambient noise, the ambient brightness, and the face position is suitable for the heart rate variability, based on a result of checking whether each of the ambient noise, the ambient brightness, and the face position is suitable for the heart rate variability measurement environment;
   by the processor, providing a questionnaire for classification of a mental state on the display in response to checking whether each of the ambient noise, the ambient brightness, and the face position is suitable for a heart rate variability measurement environment;
   by the processor, generating an image by capturing the face of the user by the camera while the user inputs an answer to the questionnaire;
   by the processor, controlling the wireless communication unit to transmit the generated image to the mental state classification server;
   by the mental state classification server, receiving the image generated from the computing device;
   by the mental state classification server, controlling to extract heart rate variability data from the generated image; and
   by the processor, controlling to display the face of the user on the display before providing the user with the questionnaire for classification of the mental state on the display and during the questionnaire.

2. The method of claim 1, wherein the generating an image by capturing the face of the user by the camera including:
   by the processor, controlling to display on the display a noise-suitable image or a noise-unsuitable image indicating whether the ambient noise is suitable or not, depending on whether the ambient noise is suitable for the heart rate variability measurement environment;
   by the processor, controlling to display a brightness-suitable image or a brightness-unsuitable image indicating whether the ambient brightness is suitable or unsuitable for the display according to whether the ambient brightness is suitable for the heart rate variability measurement environment; and
   by the processor, controlling to display on the display a face position-suitable image or a face position-unsuitable image indicating whether the face position is suitable or unsuitable for the heart rate variability measurement environment according to whether the face position is suitable for the heart rate variability measurement environment.

3. The method of claim 1, wherein the controlling to display on the display images further comprises:
   by the processor, controlling to display a notification text on the display according to whether each of the ambient noise, the ambient brightness, and the face position is suitable for the heart rate variability measurement environment.

4. The method of claim 1, wherein the providing a questionnaire for classification of a mental state comprises:
   by the processor, controlling to display a state of the face of the user including at least a middle of a forehead and both cheeks on the display while conducting a questionnaire on the mental state of the user.

5. The method of claim 1, wherein the providing a questionnaire for classification of a mental state comprises:
by the processor, generating time information by measuring a time from when the question of the questionnaire is provided on the display to when the user's answer to the question is input through the display; and
by the processor, controlling the display to display an inverse question for confirming whether the user has consistently answered the questionnaire during the questionnaire.

6. The method of claim 5, after the controlling to extract heart rate variability data, further comprising:
by the processor, determining whether the answer of the user to the questionnaire is an insincere answer based on at least one of the time information and a rate of consistently answering the inverse question.

7. The method of claim 6, after the determining whether the answer of the user to the questionnaire is an insincere answer, further comprising:
by the processor, displaying a question confirming reliability of the user's answer to the questionnaire on the display in response to the user's answer to the questionnaire determined as an insincere answer; and
by the processor, controlling the display to display notification content that induces the user to retake the questionnaire in response to an answer that the reliability of the user's answer to the questionnaire is not high is input through the display.

8. The method of claim 1, after the controlling to extract heart rate variability data, further comprising:
by the mental state classification server, obtaining a first numerical value indicating a possibility that the user corresponds to the mental state based on an answer to the questionnaire input by the user by executing a first algorithm;
by the mental state classification server, obtaining a second numerical value indicating a possibility that the user corresponds to the mental state based on the heart rate variability data of the user extracted by executing a second algorithm; and
by the mental state classification server, to obtain a third numerical value indicating a possibility that the user corresponds to the mental state based on the first numerical value and the second numerical value by executing a third algorithm.

9. A mental state classification server for classifying a mental state of a user through a user computing device, wherein the mental state classification server is configured to:
receive sound information detected by a user computing device;
receive an image captured by the user computing device and generated;
check whether each of ambient noise of the user, ambient brightness from the image, and a face position of the user in the image is suitable for a heart rate variability measurement environment, based on the received sound information and the received image;
transmit a first control signal for controlling the user computing device to the user computing device based on a result of checking whether the heart rate variability measurement environment is suitable, wherein the first control signal is a control signal that causes the user computing device to display on the display of the user computing device images indicating whether each of the ambient noise, the ambient brightness, and the face position is suitable for the heart rate variability measurement environment;
transmit a second control signal to the user computing device in response to checking that each of the ambient noise, the ambient brightness, and the face position is suitable for a heart rate variability measurement environment, wherein the second control signal causes the user computing device to display a questionnaire for classification of a mental state on the display;
receive an image generated by capturing the face of the user from the user computing device while the user inputs an answer to the questionnaire through the user computing device; and
extract heart rate variability data from the answers to the questionnaire and the received images.

10. The mental state classification server of claim 9, wherein the mental state classification server is configured to:
based on the result of checking whether the heart rate variability measurement environment is suitable, transmit a 1-1 control signal to the user computing device to display a noise-suitable image or a noise-unsuitable image indicating whether the ambient noise is suitable or not;
transmit a 1-2 control signal to the user computing device to display on the display a brightness-suitable image or brightness-unsuitable image indicating whether the ambient brightness is suitable or unsuitable;
transmit a 1-3 control signal to the user computing device to display on the display a face position-suitable image or face position-unsuitable image indicating suitability or unsuitability of the face position.

11. The mental state classification server of claim 9, wherein the mental state classification server is configured to:
based on the result of checking whether the heart rate variability measurement environment is suitable, transmit a third signal to the user computing device to display on the display a notification text indicating whether each of the ambient noise, the ambient brightness, and the face position is suitable for the heart rate variability measurement environment.

12. A computing device for classifying a user's mental state, comprising:
a microphone;
a camera;
a display; and
a processor;
wherein the microphone is configured to sense ambient noise of the user;
wherein the camera is configured to generate an image by capturing the face of the user;
wherein the processor is configured to check whether each of the ambient noise sensed by the microphone, the ambient brightness obtained from the image, and the face position obtained from the image is suitable for a heart rate variability measurement environment; control the display to display images indicating whether each of the user's ambient noise, the ambient brightness, and the face position is suitable for a heart rate variability measurement environment; display a questionnaire for classification of the user's mental state on the display in response to checking that each of the ambient noise, the ambient brightness, and the face position is suitable for the heart rate variability measurement environment; and extract a heart rate variability data from the image, which is generated by capturing the face of the user while the user inputs an answer to the questionnaire, and wherein the processor is configured to control the face of the user to be displayed on the display before displaying a questionnaire for classification of the mental state on the display and while the questionnaire is in progress.

13. The computing device of claim 12, wherein the processor is configured to control to display on the display a noise-suitable image or a noise-unsuitable image indicating whether the ambient noise is suitable or not, a brightness-suitable image or a brightness-unsuitable image indicating whether the ambient brightness is suitable or unsuitable, and a face position-suitable image or a face position-unsuitable image indicating whether the face position is suitable or unsuitable, based on the result of checking whether the heart rate variability measurement environment is suitable.

14. The computing device of claim 12, wherein the processor is configured to control the display to display on the display a notification text indicating whether each of the ambient noise, the ambient brightness, and the face position is suitable for the heart rate variability measurement environment.

15. The computing device of claim 12, wherein the processor is configured to control the display to display a progress rate of the heart rate variability measurement as a graph or numerical value while conducting a questionnaire on the mental state of the user.

* * * * *